US007001905B2

(12) United States Patent
Biwersi et al.

(10) Patent No.: US 7,001,905 B2
(45) Date of Patent: Feb. 21, 2006

(54) SUBSTITUTED DIARYLAMINES AS MEK INHIBITORS

(75) Inventors: Cathlin Biwersi, Ann Arbor, MI (US);
Haile Tecle, Ann Arbor, MI (US);
Joseph Scott Warmus, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/221,522

(22) PCT Filed: Mar. 12, 2001

(86) PCT No.: PCT/US01/07816

§ 371 (c)(1),
(2), (4) Date: Sep. 13, 2002

(87) PCT Pub. No.: WO01/68619

PCT Pub. Date: Sep. 20, 2001

(65) Prior Publication Data

US 2003/0225076 A1    Dec. 4, 2003

Related U.S. Application Data

(60) Provisional application No. 60/189,714, filed on Mar. 15, 2000, provisional application No. 60/210,205, filed on Jun. 8, 2000.

(51) Int. Cl.
C07D 265/22  (2006.01)
C07C 237/30  (2006.01)
C07C 237/32  (2006.01)
A61K 31/536  (2006.01)
A61K 31/166  (2006.01)

(52) U.S. Cl. .............................. 514/237.5; 514/237.8; 514/255.01; 514/329; 514/335; 514/352; 514/357; 514/406; 514/415; 514/423; 514/424; 514/452; 548/200; 548/338.1; 548/362.1; 548/371.7; 548/506; 548/539; 548/550; 548/568; 546/208; 546/224; 546/242; 546/226; 546/309; 544/59; 544/169; 562/456; 562/457; 562/622; 562/623

(58) Field of Classification Search ............... 548/200, 548/338.1, 362.1, 371.7, 506, 539, 550, 568; 546/208, 224, 242, 226, 309; 544/59, 169, 544/165, 391; 549/366, 493; 562/456, 457, 562/622, 623; 514/423, 424, 428, 403, 329, 514/357, 330, 227.5, 255.01, 452, 406, 352, 514/326, 237.8, 335, 400, 237.5, 415, 471, 514/365

See application file for complete search history.

(56) References Cited

U.S. PATENT DOCUMENTS

| 5,068,250 A | 11/1991 | Penning et al. |
| 5,525,625 A | 6/1996 | Bridges et al. |
| 6,310,060 B1 | 10/2001 | Barrett et al. |

FOREIGN PATENT DOCUMENTS

| WO | WO 93/24442 A1 | 12/1993 |
| WO | WO 95/22992 A2 | 8/1995 |
| WO | WO 97/07790 A1 | 3/1997 |
| WO | WO 98/37881 A1 | 9/1998 |
| WO | WO 99/01421 A1 | 1/1999 |
| WO | WO 99/01426 A1 | 1/1999 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |

OTHER PUBLICATIONS

Traxler, Protein Tyrosine Kinase inhibitors in cancer treatment, Exp. Opin. Ther. Patents, 7(6): 571-588, 1997.*
Simone, Oncology: Introduction, Cecil Textbook of Medicine, 20th Edition, vol. 1, pp. 1004-1010, 1996.*
Lonn et al., Drug treatment in heart failure, BMJ, vol. 320, pp. 1188-1192, Apr. 2000.*
Brigden, MD, M. L., "A Practical Workup for Eosinophilia," Postgraduate Medicine1999, 193-210, vol. 105, No. 3.
Duesbery, N., et al., "MEK Wars, A New Front in the Battle Against Cancer," Nature Medicine, 1999, 736-737, vol. 5, No. 7.
Duncia, J. V., et al., "MEK Inhibitors: The Chemistry and Bilogical Activity of U0126, its Analogs, and Cyclization Products," Bioorganic & Medicinal Chemistry Letters, 1998, 2839-2844, vol.8.
Ji, R., et al., "Nociceptive-Specific Activation of ERK in Spinal Neurons Contributes to Pain Hypersensitivity," Nature Neuroscience, 1999, 1114-1119, vol. 2, No. 12.
Sebolt-Leopold, J. S., et al., "Blockade of the MAP Kinase Pathway Suppresses Growth of Colon Tumors in vivo," Nature Medicine, 1999, 810-816, vol. 5, No. 7.
Sebolt-Leopold, J. S., "Development of Anticancer Drugs Targeting the MAP Kinase Pathway," Oncogene, 2000, 6594-6599, vol. 19.

* cited by examiner

Primary Examiner—Deepak Rao
(74) Attorney, Agent, or Firm—Bryan C. Zielinski; Galina M. Yakovleva

(57) ABSTRACT

Diarylamines, such as 5-amide substituted diarylamines of formula (I) or formula (II) wherein A is hydroxy, $C_{1-6}$ alkoxy, or $NR_6OR_7$; X is $OR_{12}$, $NR_{13}R_{12}$, or $NR_{14}$; inhibitors of MEK and are useful in the treatment of a variety of proliferative disease states, such as conditions related to the hyperactivity of MEK, as well as diseases modulated by the MEK cascade.

17 Claims, No Drawings

SUBSTITUTED DIARYLAMINES AS MEK INHIBITORS

This application is a 371 application of PCT/US01/07816 filed Mar. 12, 2001, which claims the benefit of priority to U.S. provisional application Ser. No. 60/189,714 filed Mar. 15, 2000 and U.S. provisional application Ser. No. 60/210,205 filed Jun. 8, 2000.

The present invention relates to diarylamines, such as 5-amide substituted diarylamines, and methods of use thereof.

BACKGROUND OF THE INVENTION

Mitogen ERK Kinase ("MEK") enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates the MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

It has been found that the compounds of the present invention are inhibitors of MEK and are useful in the treatment of a variety of proliferative disease states, such as conditions related to the hyperactivity of MEK, as well as diseases modulated by the MEK cascade.

SUMMARY

The present invention provides compounds of formula I and II:

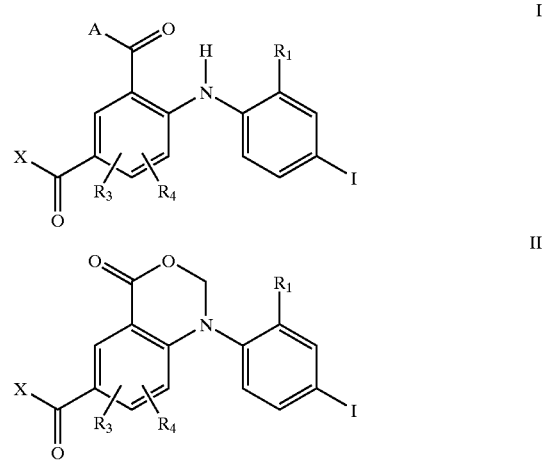

wherein
  $R_1$ is hydrogen, $C_{1-8}$ alkyl, $C_{1-8}$ alkoxy, halo, $C_{1-2}$ haloalkyl, or CN;
  $R_3$ and $R_4$ are each independently hydrogen, halo, $C_{1-2}$ haloalkyl, $C_{1-8}$ alkyl, $C_{1-8}$ alkoxy, nitro, CN, or (O or NH)$_k$—(CH$_2$)$_j$—$R_9$, where $R_9$ is hydrogen, hydroxy, $CO_2H$ or $NR_{10}R_{11}$;
  j is 0 to 4;
  k is 0 or 1;
  $R_{10}$ and $R_{11}$ are each independently hydrogen or $C_{1-8}$ alkyl, or together with the nitrogen to which they are attached form a 3- to 10-member cyclic ring optionally containing one, two, or three additional heteroatoms selected from the group consisting of O, S, NH, and N—$C_{1-8}$ alkyl;
  A is hydroxy, $C_{1-6}$ alkoxy, or $NR_6OR_7$;
  $R_6$ is hydrogen, $C_{1-8}$ alkyl, (CO)—$C_{1-8}$ alkyl, phenyl, naphthyl, phenyl($C_{1-8}$ alkyl), or $C_{3-10}$ cycloalkyl;

$R_7$ is hydrogen, $C_{1-8}$ alkyl, $C_{2-8}$ alkenyl, $C_{2-8}$ alkynyl, $C_{3-10}$ cycloalkyl or $C_{3-10}$ cycloalkyl optionally containing a heteroatom selected from the group consisting of O, S, and $NR_9$;

X is $OR_{12}$, $NR_{13}R_{12}$, or $NR_{14}$;

$R_{12}$ and $R_{13}$ are each independently hydrogen, $C_{1-6}$ alkyl, $C_{2-6}$ alkenyl, $C_{2-6}$ alkynyl, $C_{4-6}$ cycloalkyl, $[(CH_2)_nY(CH_2)_m]_qCH_3$, phenyl, naphthyl, $(C_{1-6}$ alkyl)phenyl, $—[(CH_2)_nY(CH_2)_m]_q$phenyl, $C_{2-6}$ heteroaryl, $(C_{1-6}$ alkyl)$C_{2-6}$ heterocyclic radical, or $[(CH_2)_nY(CH_2)_m]_q$ $C_{2-6}$ heterocyclic radical;

Y is N or O;

$R_{14}$ taken with N is a 5- to 7-membered heterocyclic radical with between 0 and 3 additional heteroatoms or heteroatom combinations in the ring selected from the group consisting of O, S, SO, $SO_2$, NH, and NMe; $0 \le n$, $m \le 6$, $n+m \le 8$, $1 \le q \le 5$; and wherein the above alkyl, alkenyl, alkynyl, heterocyclic radical, aryl, and cycloalkyl groups can be optionally substituted with between 1 and 4 substituents independently selected from the group consisting of hydroxy, $C_{1-4}$ alkyl, fluoro, chloro, iodo, bromo, amino, and $C_{1-4}$ alkoxy, and $NR_aR_b$;

wherein $R_a$ and $R_b$ are each independently selected from the group consisting of hydrogen and $C_{1-6}$ alkyl; and the pharmaceutically acceptable salts thereof.

The invention also provides a pharmaceutical composition comprising a compound of formula I or II and a pharmaceutically acceptable carrier.

Additionally, the invention provides a method of treating a proliferative disease in a patient in need thereof comprising administering a therapeutically effective amount of a compound of formula I or II.

The invention also provides the use of a compound of formula I or II for the manufacture of a medicament for the treatment of a proliferative disease.

Furthermore, the invention provides methods of treating cancer, restenosis, psoriasis, autoimmune disease, atherosclerosis, osteoarthritis, rheumatoid arthritis, heart failure, chronic pain, and neuropathic pain in a patient in need thereof comprising administering a therapeutically effective amount of a compound of formula I or II.

The invention also provides the use of a compound of formula I or II for the manufacture of a medicament for the treatment of cancer, restenosis, psoriasis, autoimmune disease, atherosclerosis, osteoarthritis, rheumatoid arthritis, heart failure, chronic pain, and neuropathic pain.

In addition, the invention provides a method for treating cancer in a patient in need thereof comprising administering a therapeutically effective amount of a compound of formula I or II in combination with radiation therapy or at least one chemotherapeutic agent.

The invention also features synthetic intermediates and methods disclosed herein.

Other aspects of the invention are provided in the description, examples, and claims below.

DETAILED DESCRIPTION

The invention features diarylamine compounds, pharmaceutical compositions thereof, and methods of using such compounds and compositions.

Certain terms are defined below and by their usage throughout this disclosure.

Alkyl groups, such as $C_{1-8}$ alkyl, include aliphatic chains (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, n-butyl, isobutyl, t-butyl, pentyl, isopentyl, 2,3-dimethylpropyl, hexyl, 2,3-dimethylhexyl, 1,1-dimethylpentyl, heptyl, and octyl. The term "$C_{1-8}$ alkyl" includes within its definition the terms "$C_{1-6}$ alkyl" and "$C_{1-4}$ alkyl".

Cycloalkyl groups, such as $C_{3-10}$ cycloalkyl, include cyclopropyl, cyclobutyl, cyclopentyl, cyclohexyl, cycloheptyl, and cyclooctyl. The term "$C_{3-10}$ cycloalkyl" includes within its definition the terms "$C_{4-6}$ cycloalkyl".

The term "halo" as used herein refers to fluoro, chloro, bromo, or iodo.

The term "haloalkyl" as used herein refers to a straight or branched alkyl chain with 1, 2 or 3 halo atoms attached to it. The term "$C_{1-2}$ haloalkyl" as used herein refers to a straight or branched alkyl chain having from one to two carbon atoms with 1, 2 or 3 halo atoms attached to it. Typical $C_{1-2}$ haloalkyl groups include chloromethyl, 2-bromoethyl, difluoromethyl, trifluoromethyl and the like.

The term "alcoxy" as used herein refers to a straight or branched alkyl chain attached to an oxygen atom. The term "$C_{1-8}$ alcoxy" as used herein refers to a straight or branched alkyl chain having from one to eight carbon atoms attached to an oxygen atom. Typical $C_{1-8}$ alcoxy groups include methoxy, ethoxy, propoxy, isopropoxy, butoxy, t-butoxy, pentoxy and the like. The term "$C_{1-8}$ alcoxy" includes within its definition the terms "$C_{1-6}$ alcoxy" and "$C_{1-4}$ alcoxy".

Alkyl and cycloalkyl groups can be substituted with 1, 2, 3 or more substituents which are independently selected from hydroxy, alkyl, halo, amino, alkoxy, alkylamino, dialkylamino, cycloalkyl, aryl, aryloxy, arylalkyloxy, heterocyclic radical, and (heterocyclic radical)oxy. Specific examples include fluoromethyl, hydroxyethyl, 2,3-dihydroxyethyl, (2- or 3-furanyl)methyl, cyclopropylmethyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, N-pyridinylethyl, diethylaminoethyl, and cyclobutylmethyl.

In some embodiments, each hydrocarbon radical above is optionally substituted with between 1 and 3 or more substituents independently selected from halo, hydroxyl or hydroxy, amino, (amino)sulfonyl, and $NO_2$. In another embodiment, each heterocyclic radical above is optionally substituted with between 1 and 3 or more substituents independently selected from halo, $C_{1-4}$ alkyl, $C_{3-6}$ cycloalkyl, $C_{3-4}$ alkenyl, $C_{3-4}$ alkynyl, phenyl, hydroxyl or hydroxy, $C_1–C_4$ alkoxy amino, (amino)sulfonyl, and $NO_2$, wherein each substituent alkyl, cycloalkyl, alkenyl, alkynyl or phenyl is in turn optionally substituted with between 1 and 2 substituents independently selected from halo, $C_{1-2}$ alkyl, hydroxyl or hydroxy, amino, and $NO_2$.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo-, nitro-, alkyl-, phenyl-, cycloalkyl- and so on, or combinations of substituents. According to formula I and II, therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxyalkyl, alkylaminoalkyl, dialkylaminoalkyl, arylalkyl, aryloxyalkyl, arylalkyloxyalkyl, (heterocyclic radical)alkyl, and (heterocyclic radical)oxyalkyl.

$R_1$ thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alkylaryl)alkyl, (haloaryl)alkyl, (hydroxyaryl)alkynyl, and so forth. Similarly, $R_a$ includes hydroxyalkyl and aminoaryl, and $R_b$ includes hydroxyalkyl, aminoalkyl, and hydroxyalkyl(heterocyclic radical)alkyl.

Alkenyl groups are analogous to alkyl groups, but have at least one double bond (two adjacent $sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof; like alkyl groups, unsaturated groups may be straight chain or branched, and they may be substituted as described both above for alkyl groups and throughout the disclosure by example. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4hydroxy-3-butynyl, 3-(3-fluorophenyl)-2-propynyl, and 2-methyl-2-propenyl. In formulas I and II, alkenyls and alkynyls can be $C_{2-4}$, $C_{2-6}$ or $C_{2-8}$, for example, and are preferably $C_{3-4}$ or $C_{3-8}$.

Heterocyclic radicals, which include but are not limited to heteroaryls, such as $C_{3-8}$ and $C_{2-6}$ heteroaryls, include: furyl, oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their nonaromatic counterparts. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl. Heterocyclic radicals may be substituted as described both above for alkyl groups and throughout the disclosure by example.

Heterocyclic radicals include heteroaryls such as substituted or Unsubstituted radicals of pyran, pyrazole, triazole, indazole, pyrazine, oxadiazole, oxathiadiazole; heterocycles also include heteroalkyls such as substituted and unsubstituted radicals of tetrahydropyran, pyrrolidone, imidazoline, and tetrahydrothiophene.

The present invention includes pharmaceutically acceptable salts, amides, and esters of the disclosed compounds. The invention also features a pharmaceutically acceptable salt or $C_{1-8}$ ester of a disclosed compound. For example, the disclosed alcohol compounds may form esters having the structure obtained by replacing the H of a hydroxyl group with a —C(=O)$C_{1-7}$ acyl group.

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.,* 1977, 66:1–19 which is incorporated herein by reference. Representative pharmaceutically acceptable amides of the invention include those derived from ammonia, primary $C_{1-6}$ alkyl amines and secondary di($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The present invention includes compounds having one or more functional groups (e.g., hydroxyl, amino, or carboxyl) masked by a protecting group. Examples of protecting groups used to protect functional groups and their preparation are disclosed by T. W. Green, "Protective Groups in Organic Synthesis," John Wiley & Sons, 1981. Choice of the protecting group used will depend upon the substituent to be protected and the conditions that will be employed in subsequent reaction steps wherein protection is required, and is well within the knowledge of one of ordinary skill in the art. Protecting groups include, but are not limited to, the list provided below.

Hydroxyl Protecting Groups

Hydroxyl protecting groups include: ethers, esters, and protection for 1,2- and 1,3-diols. The ether protecting groups include: methyl, substituted methyl ethers, substituted ethyl ethers, substituted benzyl ethers, silyl ethers and conversion of silyl ethers to other functional groups.

Substituted methyl ethers include: methoxymethyl, methylthiomethyl, t-utylthiomethyl, (phenyldimethylsilyl)methoxymethyl, benzyloxymethyl, p-ethoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothio-pyranyl, 4-methoxytetrahydrothiopyranyl S,S-dioxido, 1-[(2-chloro-4-methyl) phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8,8-trimethyl-4,7-ethanobenzofuran-2-yl.

Substituted ethyl ethers include: 1-ethoxyethyl, 1-(2,chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyethyl, 2-(phenylselenyl)ethyl, t-butyl, allyl, p-chlorophenyl, p-methoxyphenyl, 2,4-dinitrophenyl, and benzyl.

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenyl-methyl, p-methoxyphenyldiphenylmethyl, di(p-methoxyphenyl)phenylmethyl, tri-(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-ylmethyl)bis(4',4"-dimethoxyphenyl)-methyl, 1,1-bis(4-methoxyphenyl)1'- pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-pxylylsilyl, triphenylsilyl, diphenylmethylsilyl, and t-butylmethoxyphenylsilyl.

Ester Protecting Groups

Ester protecting groups include: esters, carbonates, assisted cleavage, miscellaneous esters, and sulfonates.

Examples of protective esters include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, and 2,4,6-trimethylbenzoate(mesitoate).

Carbonates include: methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Examples of assisted cleavage protecting groups include: 2-iodobenzoate, 4-azido-butyrate, 4-nitro4-methylpentanoate, o-(dibromomethyl)benzoate, 2-formylbenzene-sulfonate, 2-(methylthiomethoxy)ethyl carbonate, 4-(methylthiomethoxymethyl)benzoate, and 2-(methylthiomethoxymethyl)benzoate.

In addition to the above classes, miscellaneous esters include: 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N'N'-tetramethylphosphorodiamidate, N-phenylcarbamate, borate, dimethylphosphinothioyl, and 2,4-dinitrophenylsulfenate.

Protective sulfates include: sulfate, methanesulfonate(mesylate), benzylsulfonate, and tosylate.

Protection for 1,2 and 1,3-diols

The protection for 1,2 and 1,3-diols group includes: cyclic acetals and ketals, cyclic ortho esters, and silyl derivatives.

Cyclic acetals and ketals include: methylene, ethylidene, 1-t-butylethylidene, 1-phenylethylidene, (4-methoxyphenyl)ethylidene, 2,2,2-trichloroethylidene, acetonide(isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic ortho esters include: methoxymethylene, ethoxymethylene, dimethoxy-methylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Protection for the Carboxyl Group

Ester protecting groups include: esters, substituted methyl esters, 2-substituted ethyl esters, substituted benzyl esters, silyl esters, activated esters, miscellaneous derivatives, and stannyl esters.

Substituted methyl esters include: 9-fluorenylmethyl, methoxymethyl, methylthiomethyl, tetrahydropyranyl, tetrahydrofuranyl, methoxyethoxymethyl, 2-(trimethylsilyl)ethoxy-methyl, benzyloxymethyl, phenacyl, p-bromophenacyl, α-methylphenacyl, p-methoxyphenacyl, carboxamidomethyl, and N-phthalimidomethyl.

2-Substituted ethyl esters include: 2,2,2-trichloroethyl, 2-haloethyl, 1-chloroalkyl, 2-(trimethylsily)ethyl, 2-methylthioethyl, 1,3-dithianyl-2-methyl, 2(p-nitrophenylsulfenyl)-ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsily)-2-buten-1-yl, cinnamyl, α-methylcinnamyl, phenyl, p-(methylmercaptoyphenyl, and benzyl.

Substituted benzyl esters include: triphenylmethyl, diphenylmethyl, bis(o-nitrophenyl)methyl, 9-anthrylmethyl, 2-(9, 10-dioxo)anthrylmethyl, 5-dibenzo-suberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl esters include: trimethylsilyl, triethylsilyl, t-butyldimethylsilyl, i-propyldimethylsilyl, phenyldimethylsilyl, and di-t-butylmethylsilyl.

Miscellaneous derivatives includes: oxazoles, 2-alkyl-1, 3-oxazolines, 4-alkyl-5oxo-1,3-oxazolidines, 5-alkyl-4-oxo-1,3-dioxolanes, ortho esters, phenyl group, and pentaaminocobalt(III) complex.

Examples of stannyl esters include: triethylstannyl and tri-n-butylstannyl.

Amides and Hydrazides

Amides include: N,N-dimethyl, pyrrolidinyl, piperidinyl, 5,6-dihydrophenanthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

Protection for the Amino Group

Carbamates include: carbamates, substituted ethyl, assisted cleavage, photolytic cleavage, urea-type derivatives, and miscellaneous carbamates.

Carbamates include: methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydro-thioxanthyl)]methyl, and 4-methoxyphenacyl.

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'-and 4'-pyridyl)ethyl, 2-(N,N-icyclohexylcarboxamido)-ethyl, t-butyl, 1-adamantyl, vinyl, allyl, 1-isopropylallyl, connamyl, 4-nitrocinnamyl, quinolyl, N-hydroxypiperidinyl, alkyldithio, benzyl, p-methoxybenzyl, p-nitrobenzyl, p-bromobenzyl, p-chlorobenzyl, 2,4dichlorobenzyl, 4-methylsulfinylbenzyl, 9-anthrylmethyl, and diphenylmethyl.

Protection via assisted cleavage includes: 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2cyanoethyl, m-chloro-p-acyloxybenzyl, p-(dihydroxyboryl)benzyl, 5-benzisoxazolyl-methyl, and 2-(trifluoromethyl)-6-chromonylmethyl.

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Examples of urea-type derivatives include: phenothiazinyl-(10)-carbonyl derivative, N'-p-toluenesulfonylaminocarbonyl, and N'-phenylaminothiocarbonyl.

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxycarbonylvinyl, o-(N,N-dimethyl-carboxamido)-benzyl, 1,1-dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenyl-azo)benzyl, 1-methylcyclobutyl, 1-methylcyclohexyl, 1-methyl-1-cyclopropyl-methyl, 1-methyl-(3,5-dimethoxyphenyl)ethyl, 1-methyl-1(p-henylazophenyl)-ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Amides

Amides includes: N-formyl, N-acetyl, N-chloroacetyl, N-trichloroacetyl, N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted cleavage groups include: N-o-nitrophenylacetyl, N-o-nitrophenoxyacetyl, N-acetoacetyl, (N'-dithiobenzyloxycarbonylamino)acetyl, N-3-(p-hydroxphenyl)propionyl, N-3-(o-nitrophenyl)propionyl, N-2-methyl-2-(o-nitrophenoxy)propionyl, N-2-methyl-2-(o-phenylazophenoxy) propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic imide derivatives include: N-phthalimide, N-dithiasuccinoyl, N-2,3-diphenyl-maleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Protective groups for —NH include: N-alkyl and N-aryl amines, imine derivatives, enamine derivatives, and N-hetero atom derivatives (such as N-metal, N—N, N—P, N—Si, and N—S), N-sulfenyl, and N-sulfonyl.

N-alkyl and N-aryl amines include: N-methyl, N-allyl, N-[2-(trimethylsilyl)ethoxyl]-methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine derivatives include: N-1,1-dimethylthiomethylene, N-benzylidene, N-p-methoxybenzylidene, N-diphenylmethylene, N-[(2-pyridyl)mesityl]methylene, N(N',N'-dimethylaminomethylene), N,N'-isopropylidene, N-p-nitrobenzylidene, N-salicylidene, N-5-chlorosalicylidene, N-(5-chloro-2-hydroxyphenyl)phenyl-methylene, and N-cyclohexylidene.

An example of an enamine derivative is N-(5,5-dimethyl-3-oxo-1-cyclohexenyl).

N-metal derivatives include: N-borane derivatives, N-diphenylborinic acid derivative, N-[phenyl(pentacarbonylchromium- or -tungsten)]carbenyl, and N-copper or N-zinc chelate. Examples of N—N derivatives include: N-nitro, N-nitroso, and N-oxide. Examples of N—P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl, Examples of N-sulfenyl derivatives include: N-benzenesulfenyl, N-o-nitrobenzenesulfenyl, N-2,4-dinitrobenzenesulfenyl, N-pentachlorobenzenesulfenyl, N-2-nitro-4-methoxy-benzenesulfenyl, N-triphenylmethylsulfenyl, and N-3-nitropyridinesulfenyl. N-sulfonyl derivatives include: N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzene-sulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilylethanesulfonyl, N-9-anthracenesulfonyl, N-4-(4',8'-dimethoxynaphthylmethyl)-benzenesulfonyl, N-benzylsulfonyl, N-trifluoromethylsulfonyl, and N-phenacylsulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

Some of these masked or protected compounds are pharmaceutically acceptable; others will be useful as intermediates. Synthetic intermediates and processes disclosed herein, and minor modifications thereof, are also within the scope of the invention.

The compounds of formulas I and II can be prepared by techniques and procedures readily available to one of ordinary skill in the art, for example by following the procedures as set forth in the following Schemes or analogous variants thereof. These synthetic strategies are further exemplified in Examples 1–6 below. These Schemes are not intended to limit the scope of the invention in any way.

As used herein, the following terms have the meanings indicated: "LiBH$_4$" refers to lithium borohydride; "TMSCI"

refers to trimethylsilyl chloride; "TBDPSCl" refers to tert-butyldiphenylsilyl chloride; "sBuLi" refers to sec-butyllithium; "TBAF" refers to tetrabutylammonium fluoride; "HOAc" refers to acetic acid; "KMnO₄" refers to potassium permanganate; "LiHMDS" refers to lithium 1,1,1,3,3,3-hexamethyl-disilazane. All other terms and substituents, unless otherwise indicated, are previously defined. The reagents and starting materials are readily available to one of ordinary skill in the art. Scheme I provides a synthesis of the compound of structure (2).

SCHEME I

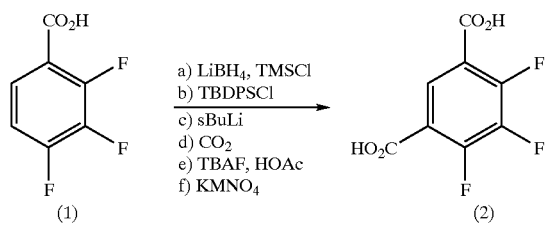

In Scheme I, step a, the compound of structure (1), which is 2,3,4-trifluorobenzoic acid, is reduced with in situ prepared borane under conditions described in *Angew. Chem. Int. Ed.* (1989), 28, 218 to provide the corresponding alcohol.

In Scheme I, step b, the alcohol is protected with a suitable hydroxyl protecting group, such as tert-butyldiphenylsilyl chloride. A suitable hydroxyl protecting group will be stable to basic conditions.

In Scheme I, step c, directed metallation of the protected alcohol provides the anion. In step d, the resulting anion is quenched with carbon dioxide to provide the monoacid.

In Scheme I, steps e and f, the protected monoacid is deprotected and oxidized under conditions well known in the art to provide the symmetrical diacid (2) which is 4,5,6-trifluoro-isophthalic acid.

These synthetic strategies are further exemplified in Example 1, steps a–d.

Scheme II provides a synthesis of the compound of structure (4).

SCHEME II

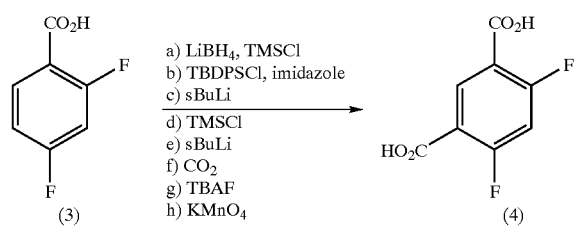

In Scheme II, step a, the compound of structure (3), which is 2,4-difluorobenzoic acid, is reduced with in situ prepared borane under conditions described in *Angew. Chem. Int. Ed.* (1989), 28, 218 to provide the corresponding alcohol.

In Scheme II, step b, the alcohol is protected with a suitable hydroxyl protecting group, such as tert-butyldiphenylsilyl chloride. A suitable hydroxyl protecting group will be stable to basic conditions.

In Scheme II, step c, directed metallation of the protected alcohol provides the anion. In step d, the resulting anion is quenched with a silylating agent, such as trimethylsilyl chloride to provide the monoacid.

In Scheme II, step e, directed metallation of the protected alcohol provides the anion. In step f, the resulting anion is quenched with carbon dioxide to provide the monoacid.

In Scheme II, steps g and h, the protected monoacid is deprotected and oxidized under conditions well known in the art to provide the symmetrical diacid (4) which is 4,6-difluoroisophthalic acid.

Scheme III provides a synthesis of the compounds of formula I, which includes formulas Ia and Ib, and formula II.

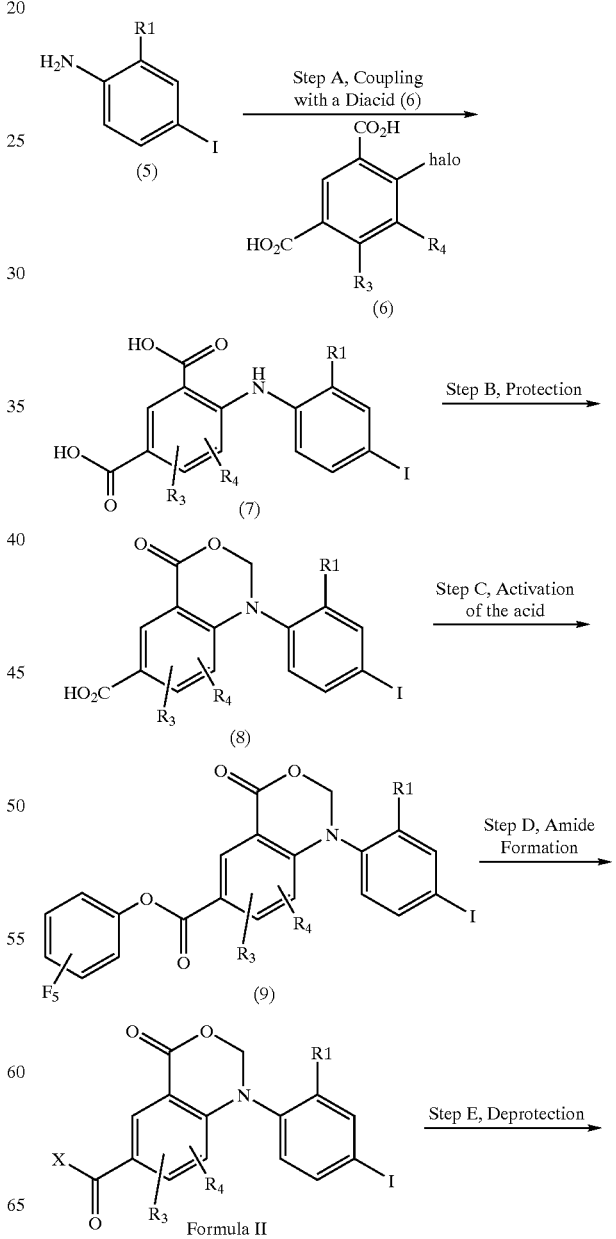

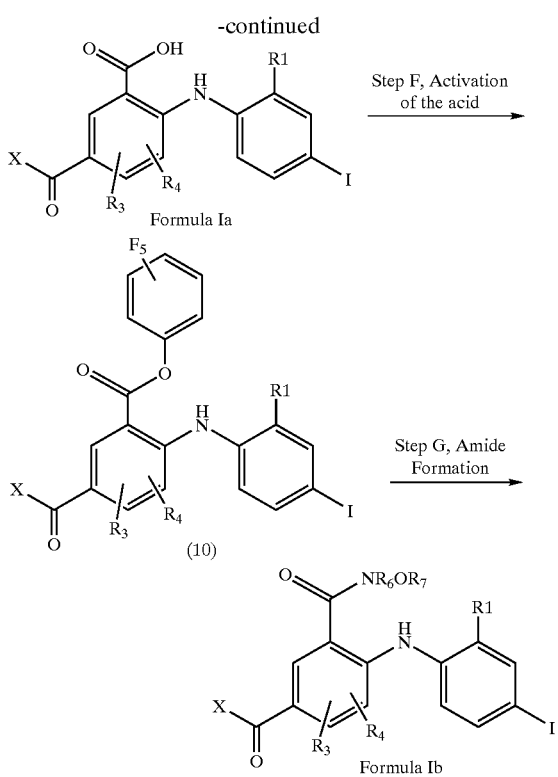

In Scheme III, step A, a suitable aniline (5), such as 4-iodo-2 methylaniline, 4-iodo-2-chloroaniline, or 4-iodo-2-fluoroaniline is coupled with a symmetrical diacid (6) to provide the compound of structure (7). Examples of suitable diacids (6) include, but are not limited to, compound (2) as shown in Scheme I, compound (4) as shown in Scheme II and 4-fluoro-isophthalic acid which can be prepared by one of ordinary skill in the art following generally the procedure disclosed by Chuprina. G. N. et al., Uzh. Vses. Khim. O-va, 19(5), 598–9 (1974). It is within the skill of one of ordinary art to identify additional diacids (6) useful in the preparation of compounds of the present invention. For example, compound (6) and compound (5), in separate flasks, are each suspended in a suitable organic solvent, such as tetrahydrofuran, at −78° C. under nitrogen. Each suspension is treated with an excess of a suitable base, such as 2 equivalents of lithium 1,1,1,3,3,3-hexamethyl-disilazane or lithium amide. After both solutions are stirred for about 30 minutes at −78° C., the diacid solution was transferred by cannula into the aniline solution and allowed to warm to room temperature. After stirring from about 4 to 12 hours, the mixture was precipitated with a suitable solution, such as a saturated HCl diethyl ether solution or combined with 1N HCl and extracted with ethyl acetate. The resulting precipitate was filtered and concentrated under vacuum to provide the anthranilic diacid (7).

In Scheme III, step B, the acidic groups of the diacid (7) are differentiated by protection using suitable aldehyde, such as formalin or paraformaldehyde when R1 is methyl; or by using methyl bromide and cesium fluoride when R1 is a halogen, such as chloride or fluoride. For example, the diacid (7), a suitable aldehyde, such as paraformaldehyde, and a suitable acid, such as para-toluenesulfonic acid monohydrate were combined in a suitable solvent, such as dichloromethane. In a roundbottom flask attached with a Dean-Stark apparatus, the solution is allowed to reflux for about 3 hours. The resulting solution is concentrated and the residue is suspended in a suitable solvent, such as methanol. The aldehyde is filtered off, the filtrate is collected and concentrated under vacuum to provide the free acid (8).

In Scheme III, step C, the free acid (8) is activated, such as by the addition of trifluoroacetic acid pentafluorophenyl ester. For example, to a suspension of the free acid (8) in a suitable solvent, such as in N,N-dimethylformamide is added trifluoroacetic acid pentafluorophenyl ester and a suitable base, such as pyridine. The reaction mixture is stirred for about 4 hours, diluted with a suitable solvent, such as ethyl acetate, and washed with a series of solutions, such as 3 times with 1.0 M HCl solution, 3 times with 5% aqueous NaHCO$_3$ solution, 2 times with water and once with saturated brine solution. The organic extracts are combined, dried over sodium sulfate, filtered and concentrated under vacuum to provide the activated free ester (9).

In Scheme III, step D, amines are added to the free ester (9) to provide the amide or the ester, which is a compound of formula II. For example, the free ester (9) is suspended in a suitable solvent, such as tetrahydrofuran. To the resulting suspension, a suitable alcohol, such as methanol, or suitable amines, such as methylamine hydrochloride and a suitable tertiary amine base, such as triethylamine and N,N-diisopropylethylamine are added. After stirring from about 12 to 17 hours, the reaction mixture was diluted with a suitable solvent, such as ethyl acetate and washed using a series of solutions, such as 2 times with water and 2 times with saturated brine solution. The organic extracts are combined, dried over sodium sulfate, filtered and concentrated under vacuum to provide the amide of formula II.

Examples of X may be derived by one of ordinary skill in the art from commercially available reagents that include, but are not limited to, the following:

| | |
|---|---|
| trans-2-aminocyclohexanol hydrochloride | 2-amino-5-mercapto-1,3,4-thiadiazole |
| 2-amino-1,3,4-thiadiazole | 2-amino-5-methyl-1,3,4-thiadiazole |
| 3-amino-1-phenyl-2-pyrazolin-5-one | 2-amino-5-ethyl-1,3,4-thiadiazole |
| 5-amino-3-methylisoxazole | 2-amino-6-methoxybenzothiazole |
| 3-amino-5-methylisoxazole | 2-amino-6-ethoxybenzothiazole |
| 5-amino-3-phenyl-1,2,4-thiadiazole | 2-amino-6-methylbenzothiazole |
| 2-(2-aminoethyl)-1-methylpyrrolidine | 2-amino-4-methylbenzothiazole |
| 2-(aminomethyl)-1-ethylpyrrolidine | 4-aminobenzo-2,1,3-thiadiazole |
| 1-(2-aminoethyl)pyrrolidine | 4-amino-6-chloro-2-methylmercaptopyrimidine |
| pseudothiohydantoin | 2-aminopyrimidine |
| 1-(3-aminopropyl)-2-pyrrolidinone | 2-amino-4,6-dihydroxypyrimidine |
| furfurylamine | 4-aminopyrimidine |
| 1-aminomethyl-1-cyclohexanol hydrochloride | aminopyrazine |
| histamine | 4-morpholinoaniline |
| 3-amino-1,2,4-triazole | 4-(2-aminoethyl)morpholine |
| 3-amino-5-mercapto-1,2,4-triazole | n-(3-aminopropyl)morpholine |
| 3-amino-5-methylthio-1,2,4-triazole | 5-amino-2-chloropyridine |
| 3-aminopyrazole | 5-amino-2-methoxypyridine |
| 3-amino-4-carbethoxypyrazole | 2-aminopyridine |
| 2-amino-2-thiazoline | 2-aminopyridine |
| 2-aminothiazole | 2-(aminomethyl)pyridine |
| 2-amino-4-methylthiazole | 2-(2-aminoethyl)pyridine |
| ethyl 2-amino-4-thiazoleacetate | 3-aminopyridine |
| d-cycloserine | 3-(aminomethyl)pyridine |
| tetrahydrofurfurylamine | 4-aminopyridine |
| thiophene-2-methylamine | 4-(aminomethyl)pyridine |
| 2-aminopurine | 3-amino-1,2,4-triazine |
| 2-aminobenzimidazole | 1-(2-aminoethyl)piperidine |
| 5-methoxytryptamine | 3,4-ethylenedioxyaniline |
| 6-methoxytryptamine | 2-aminophenethyl alcohol |
| 6-aminoindazole | N,N-dimethyl-p-phenylenediamine |
| 8-azaadenine | N,N-diethyl-1,4-phenylenediamine |

-continued

| | |
|---|---|
| 2-aminobenzothiazole | 2-aminobenzenesulfonamide |
| 2-(2-aminoethoxy)ethanol | sulfanilamide |
| 2-(3,4-dimethoxyphenyl)ethylamine | 2-amino-1-methoxypropane |
| 3-isopropoxypropylamine | dl-2-amino-1-propanol |
| methyl 3-aminothiophene-2-carboxylate | 4-hydroxypiperidine |
| n-(3-aminopropyl)imidazole | 4-piperidineethanol |
| 3-aminopyrazine-2-carboxylic acid methyl ester | 1-methyl-4-(methylamino)piperidine |
| 5-amino-1-ethylpyrazole | N-methyl-p-anisidine |
| 3-amino-5-hydroxypyrazole | methylaminoacetaldehyde dimethylacetal |
| 2-amino-5-(ethylthio)-1,3,4-thiadiazole | (S)-(+)-2-(methoxymethyl)pyrrolidine |
| dl-cycloserine | 1-methylpiperazine dihydrochloride |
| 3-amino-5-methylpyrazole | 3-hydroxypiperidine hydrochloride |
| 4-chloro-n-methylaniline | dl-nornicotine |
| 2-(methylamino)ethanol | 4-hydroxypiperidine hydrochloride |
| N,N'-bis(2-hydroxyethyl)ethylenediamine | 4-(1-pyrrolidinyl)piperidine |
| diethanolamine | N-ethylpiperazine |
| 2-(butylamino)ethanethiol | d-prolinol |
| thiazolidine | thialdine |
| l-prolinol | (R)-3-hydroxypyrrolidine |
| 3-pyrrolidinol | (R)-(−)-3-pyrrolidinol hydrochloride |
| N-omega-methyltryptamine | (R)-(+)-3-hydroxypiperidine hydrochloride |
| piperazine | (S)-3-hydroxypyrrolidine |
| 1-formylpiperazine | thialdine |
| 1-methylpiperazine | |
| 1-benzylpiperazine | |
| N-(2-hydroxyethyl)piperazine | |
| morpholine | |
| thiomorpholine | |
| 2-piperidinemethanol | |
| 2-piperidineethanol | |
| 3-piperidinemethanol | |

In Scheme II, step E, the acid of the compound of formula II is deprotected under acidic conditions using a polymer bound glycol as a quench reagent to provide the compound of formula Ia. For example, to a suspension of formula II in a suitable solvent, such as tetrahydrofuran, is added a suitable quench agent, such as polymer bound glycerol, and a suitable acidic solution, such as about 10 mL of 1.0 M hydrochloric acid solution. After stirring for about 48 hours at room temperature, the resin is filtered off and the filtrate is transferred to a separatory funnel and partitioned with a suitable solvent, such as ethyl acetate. The organics are washed using a series of solutions, such as twice with 1.0 M HCl and twice with saturated brine solution. The organic extracts are collected, dried over sodium sulfate, filtered and concentrated under vacuum to provide the compound of formula Ia.

In Scheme III, step F, the deprotected acid of formula Ia is activated, such as by the addition of trifluoroacetic acid pentafluorophenyl ester and reacted with an appropriately substituted hydroxyl amine, to allow the formation of the hydroxamate, which is the compound of formula 1b. For example, to a suspension of formula 1a in a suitable solvent, such as in N,N-dimethylformamide is added trifluoroacetic acid pentafluorophenyl ester and a suitable base, such as pyridine. The reaction mixture is stirred for about 17 hours, diluted with a suitable solvent, such as ethyl acetate, and washed using a series of solutions, such as 3 times with 1.0 M HCl solution, 3 times with 5% aqueous $NaHCO_3$ solution, 2 times with water and once with saturated brine solution. The organic extracts are combined, dried over sodium sulfate, filtered and concentrated under vacuum to provide the activated free ester (10).

In Scheme III, step G, amines are added to the free ester (10) to provide the amide, which is a compound of formula Ib. For example, the free ester (10) is suspended in a suitable solvent, such as tetrahydrofuran. To the resulting suspension, a suitable alcohol, such as methanol, or suitable amines, such as methylamine hydrochloride and cyclopropylmethylamine hydrochloride, and a suitable tertiary amine base, such as triethylamine and N,N-diisopropylethylamine are added. After stirring from about 12 to 17 hours, the reaction mixture was partitioned between a suitable solvent, such as ethyl acetate and a suitable acid, such as 1.0 M HCl solution. The organic layer was washed using a series of solutions, such as 2 times with water and 2 times with saturated brine solution. The organic extracts are combined, dried over magnesium sulfate, filtered and concentrated under vacuum to provide the hydroxamate of formula Ib.

One aspect of the invention features the disclosed compounds shown in formulas I and II. Preferred compounds of formulas I or II are those in which $R_1$ is $C_{1-8}$ alkyl or halo, preferably $C_{1-8}$ alkyl, more preferably fluoro, chloro, or methyl, and most preferably methyl; R3 and R4 are each independently hydrogen or halo, preferably fluoro; A is hydroxy or $NR_6OR_7$; X is $NR_{13}R_{12}$ or $NR_{14}$; and $R_{12}$ and $R_{13}$ are each independently $[(CH_2)_nY(CH_2)_m]_qCH_3$, $(C_{1-6}$ alkyl)phenyl, $-[(CH_2)_nY(CH_2)_m]_q$phenyl, or $(C_{1-6}$ alkyl) $C_{2-6}$ heterocyclic radical.

Also preferred are compounds of formula I or formula II in which heterocyclic radicals include heteroaryls such as substituted or unsubstituted radicals of pyrrole, furan, pyran, thiophene, pyrazole, imidazole, triazole, tetrazole, indole, isoxazole, indazole, pyridine, pyrazine, oxazole, thiazole, oxadiazole, oxathiadiazole; heterocycles also include heteroalkyls such as substituted and unsubstituted radicals of morpholine, piperidine, piperazine, tetrahydrofuran, tetrahydropyran, pyrrolidone, imidazoline, and tetrahydrothiophene.

Table I and Table II provide examples of preferred compounds of the present invention.

TABLE I

| —A | —$R_1$ | —X |
|---|---|---|
| —OH | -Me | —$NH_2$ |
| —OH | -Me | —NHMe |
| —OH | -Me | —$NMe_2$ |
| —OH | -Me | —NH—(CH₂)₃—N(morpholine) |

TABLE I-continued

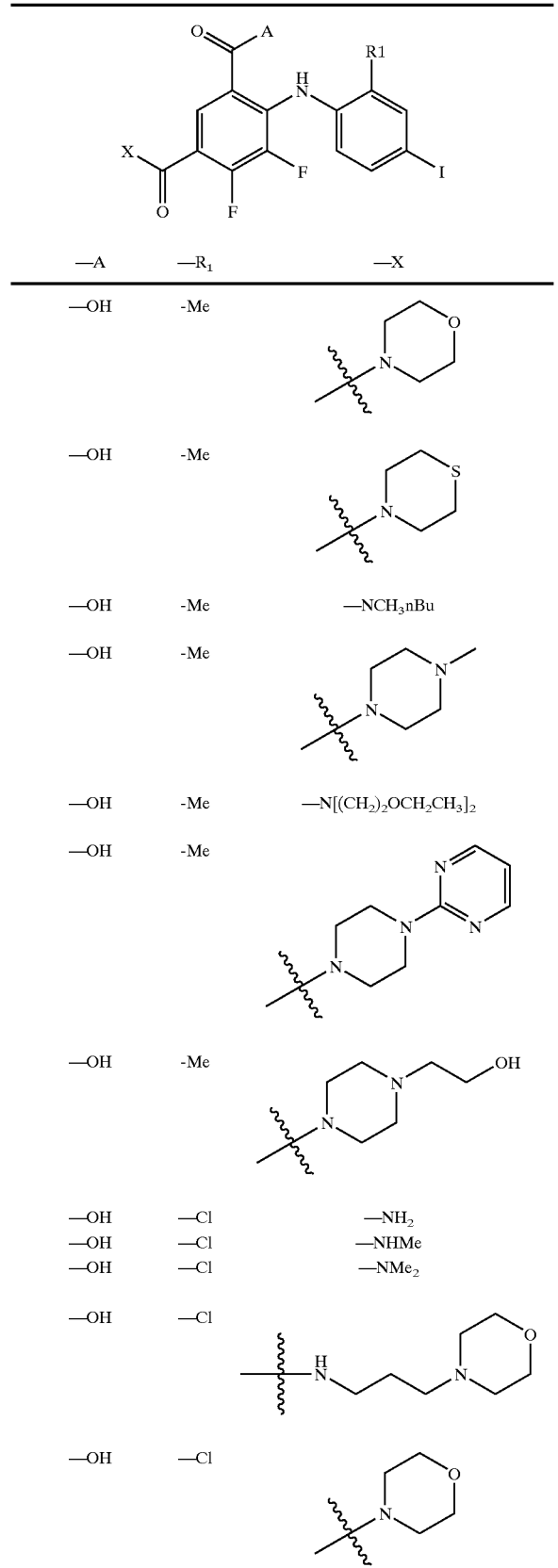

| —A | —R1 | —X |
|---|---|---|
| —OH | -Me | (morpholine) |
| —OH | -Me | (thiomorpholine) |
| —OH | -Me | —NCH₃nBu |
| —OH | -Me | (N-methylpiperazine) |
| —OH | -Me | —N[(CH₂)₂OCH₂CH₃]₂ |
| —OH | -Me | (N-pyrimidinylpiperazine) |
| —OH | -Me | (N-hydroxyethylpiperazine) |
| —OH | —Cl | —NH₂ |
| —OH | —Cl | —NHMe |
| —OH | —Cl | —NMe₂ |
| —OH | —Cl | (N-propylmorpholine amine) |
| —OH | —Cl | (morpholine) |

TABLE I-continued

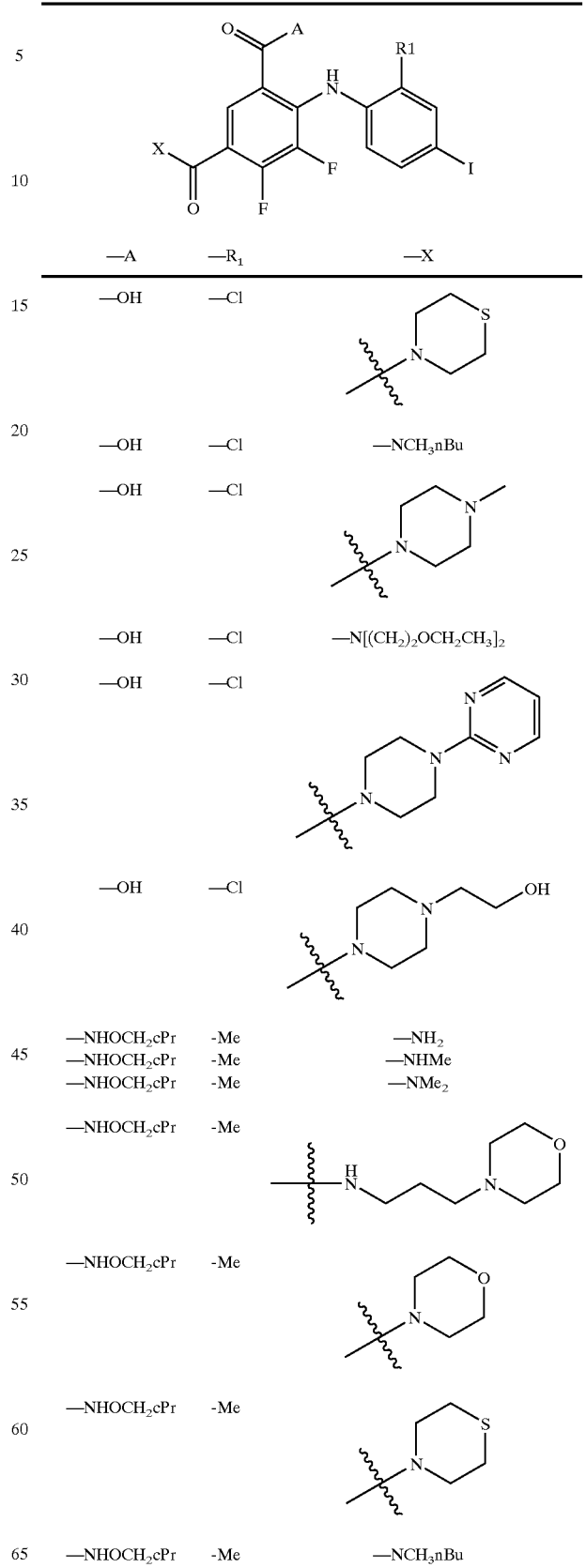

| —A | —R1 | —X |
|---|---|---|
| —OH | —Cl | (thiomorpholine) |
| —OH | —Cl | —NCH₃nBu |
| —OH | —Cl | (N-methylpiperazine) |
| —OH | —Cl | —N[(CH₂)₂OCH₂CH₃]₂ |
| —OH | —Cl | (N-pyrimidinylpiperazine) |
| —OH | —Cl | (N-hydroxyethylpiperazine) |
| —NHOCH₂cPr | -Me | —NH₂ |
| —NHOCH₂cPr | -Me | —NHMe |
| —NHOCH₂cPr | -Me | —NMe₂ |
| —NHOCH₂cPr | -Me | (N-propylmorpholine amine) |
| —NHOCH₂cPr | -Me | (morpholine) |
| —NHOCH₂cPr | -Me | (thiomorpholine) |
| —NHOCH₂cPr | -Me | —NCH₃nBu |

TABLE I-continued

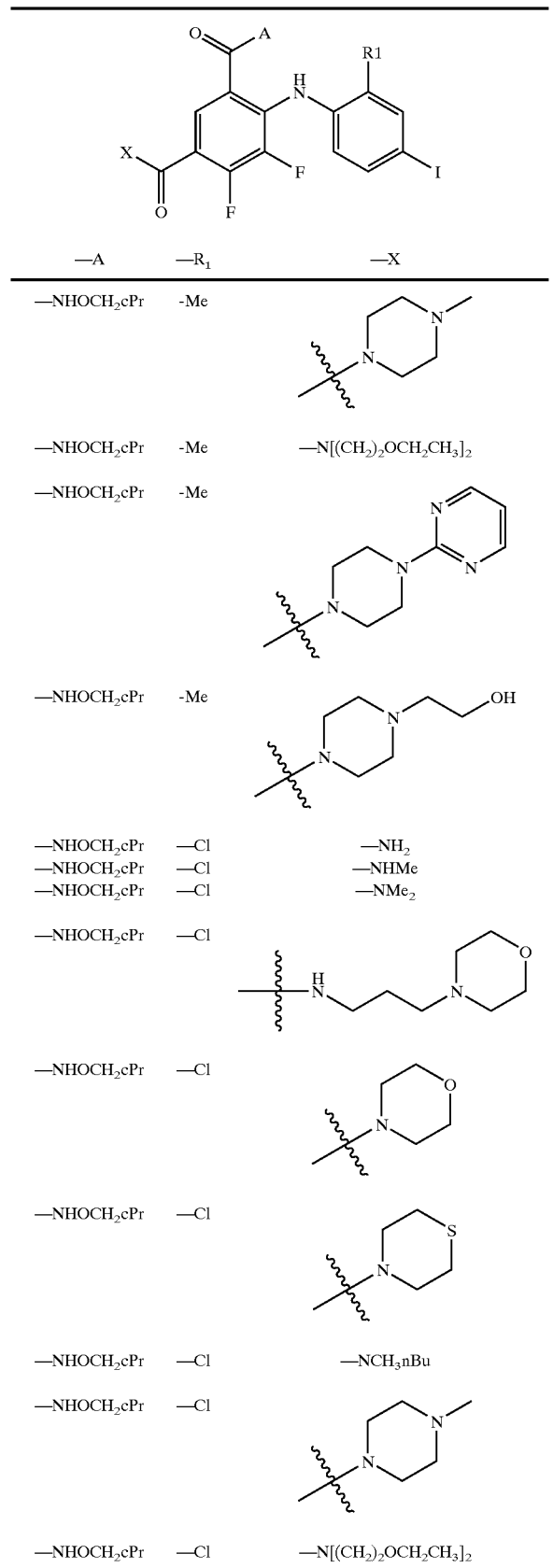

| —A | —R₁ | —X |
|---|---|---|
| —NHOCH₂cPr | -Me | N-methylpiperazinyl |
| —NHOCH₂cPr | -Me | —N[(CH₂)₂OCH₂CH₃]₂ |
| —NHOCH₂cPr | -Me | 4-(pyrimidin-2-yl)piperazinyl |
| —NHOCH₂cPr | -Me | 4-(2-hydroxyethyl)piperazinyl |
| —NHOCH₂cPr | —Cl | —NH₂ |
| —NHOCH₂cPr | —Cl | —NHMe |
| —NHOCH₂cPr | —Cl | —NMe₂ |
| —NHOCH₂cPr | —Cl | 3-morpholinopropylamino |
| —NHOCH₂cPr | —Cl | morpholinyl |
| —NHOCH₂cPr | —Cl | thiomorpholinyl |
| —NHOCH₂cPr | —Cl | —NCH₃nBu |
| —NHOCH₂cPr | —Cl | 4-methylpiperazinyl |
| —NHOCH₂cPr | —Cl | —N[(CH₂)₂OCH₂CH₃]₂ |

TABLE I-continued

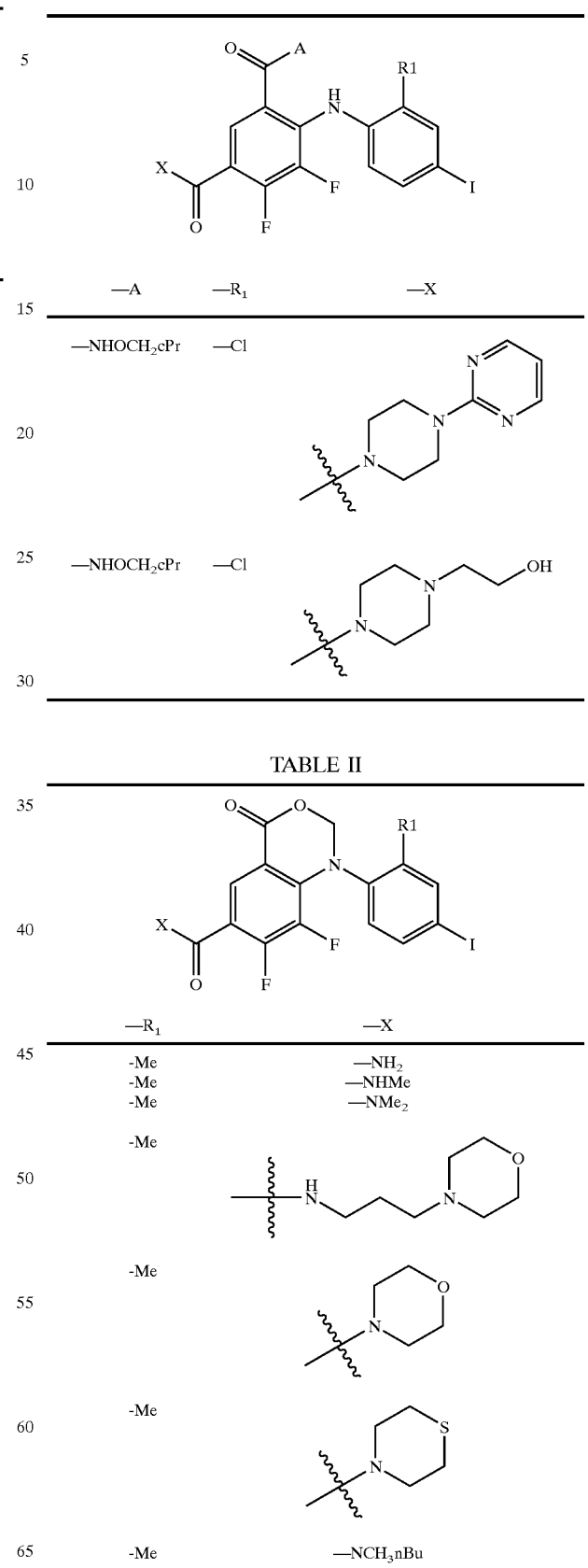

| —A | —R₁ | —X |
|---|---|---|
| —NHOCH₂cPr | —Cl | 4-(pyrimidin-2-yl)piperazinyl |
| —NHOCH₂cPr | —Cl | 4-(2-hydroxyethyl)piperazinyl |

TABLE II

| —R₁ | —X |
|---|---|
| -Me | —NH₂ |
| -Me | —NHMe |
| -Me | —NMe₂ |
| -Me | 3-morpholinopropylamino |
| -Me | morpholinyl |
| -Me | thiomorpholinyl |
| -Me | —NCH₃nBu |

TABLE II-continued

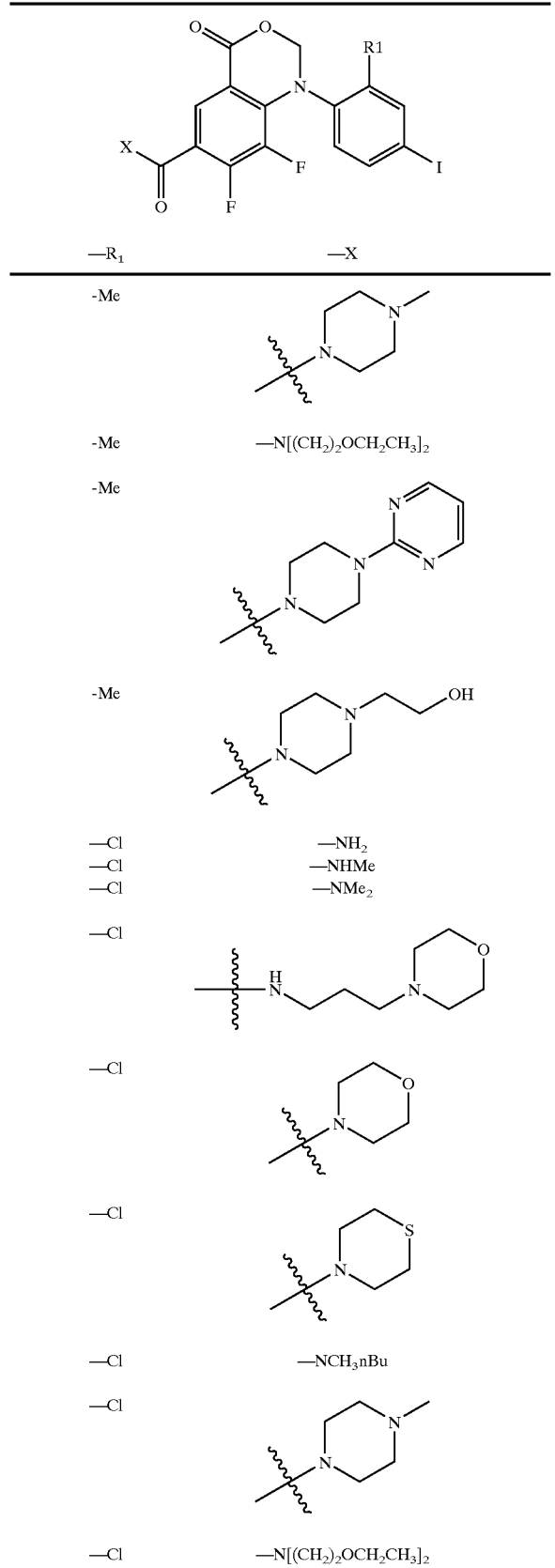

| —R₁ | —X |
|---|---|
| -Me | (N-methylpiperazine) |
| -Me | —N[(CH₂)₂OCH₂CH₃]₂ |
| -Me | (pyrimidinyl piperazine) |
| -Me | (hydroxyethyl piperazine) |
| —Cl | —NH₂ |
| —Cl | —NHMe |
| —Cl | —NMe₂ |
| —Cl | (morpholinopropyl amine) |
| —Cl | (morpholine) |
| —Cl | (thiomorpholine) |
| —Cl | —NCH₃nBu |
| —Cl | (N-methylpiperazine) |
| —Cl | —N[(CH₂)₂OCH₂CH₃]₂ |

TABLE II-continued

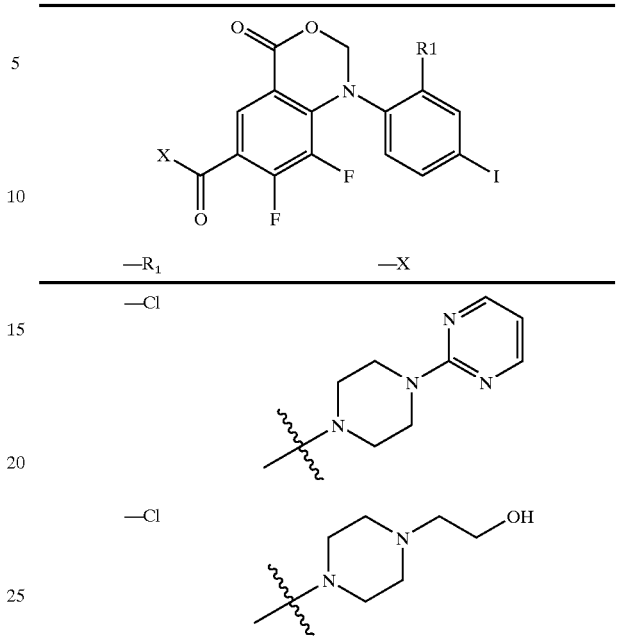

| —R₁ | —X |
|---|---|
| —Cl | (pyrimidinyl piperazine) |
| —Cl | (hydroxyethyl piperazine) |

As used herein, the term "patient" refers to any warm-blooded animal such as, but not limited to, a human, horse, dog, guinea pig, or mouse. Preferably, the patient is human.

The term "treating" for purposes of the present invention refers to prophylaxis or prevention, amelioration or elimination of a named condition once the condition has been established.

According to one aspect of the invention, the compounds are MEK inhibitors. MEK inhibition assays include the in vitro cascade assay for inhibitors of MAP kinase pathway described at column 6, line 36 to column 7, line 4 of U.S. Pat. No. 5,525,625 and the in vitro MEK assay at column 7, lines 4–27 of the same patent, the entire disclosure of which is incorporated by reference (see also Examples 163–173 below).

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a pharmaceutically or therapeutically effective amount of a disclosed compound or pharmaceutical composition thereof.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, post-operative pain, arthritis pain, and nerve injury between the peripheral nervous system and the central nervous system.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount will be between about 0.1 and about 1000 mg/kg per day, preferably between about 1 and about 300 mg/kg body weight, and daily dosages will be between about 10 and about 5000 mg for an adult subject of normal weight. Commercially available capsules or other formulations (such as liquids and film-coated tablets) of 100 mg, 200 mg, 300 mg, or 400 mg can be administered according to the disclosed methods.

The compounds of the present invention are preferably formulated prior to administration. Therefore, another aspect of the present invention is a pharmaceutical composition comprising a compound of formulas I or II and a pharmaceutically acceptable carrier. In making the compositions of the present invention, the active ingredient, such as a compound of formula I or formula II, will usually be mixed with a carrier, or diluted by a carrier or enclosed within a carrier. Dosage unit forms or pharmaceutical compositions include tablets, capsules, pills, powders, granules, aqueous and nonaqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

The following examples represent typical syntheses of the compounds of formula I and II as described generally above. These examples are illustrative only and are not intended to limit the invention in any way. The reagants and starting materials are readily available to one of ordinary skill in the art. As used herein, the following terms have the meanings indicated: "g" refers to grams; "mg" refers to milligrams; "mL" refers to milliliters; "mmol" refer to millimoles; "° C." refers to degrees Celsius; "APCI" refers to atmospheric pressure chemical ionization; and "THF" refers to tetrahydrofuran;

EXAMPLE 1

7,8-Difluoro-1-(4-iodo-2-methyl-phenyl)-4-oxo-1,4-dihydro-2H-benzo[d][1,3]oxazine-6-carboxylic acid Step a: To a suspension of (2,3,4-trifluoro-phenyl)-methanol (prepared as in *Angew. Chem. Int. Ed.* (1989), 28,218) (8.7 g, 54 mmol) in 50 mL of dichloromethane was added tert-butyldiphenylsilyl chloride (15.4 mL, 59 mmol) and imidazole (4.02 g, 59 mmol). After 17 hours, the reaction was poured into 100 mL of 1 M HCl solution and extracted into dichloromethane. The organic layer was washed 2 times with 1 M HCl solution and 2 times with brine solution. The organic phase was collected and dried over $Na_2SO_4$, filtered, and concentrated in vacuo. The white, oily solid (18.8 g) was purified by column silica chromatography eluting with 9:1 hexane:ethyl acetate to afford 14.37 g (68.5%) teft-butyl-diphenyl-(2,3,4-trifluoro-benzyloxy)-silane.

Step b: To a suspension of tert-butyl-diphenyl-(2,3,4-trifluoro-benzyloxy)-silane (7.42 g, 18.5 mmol) in freshly distilled tetrahydrofuran (50 mL) at −78° C. under nitrogen is added 1.3 M sec-butyllithium in cyclohexane (18.5 mL, 24.0 mmol). The reaction was allowed to stir at −78° C. for 1 hour and quenched with $CO_2$ gas (lecture bottle) directly into the solution for 30. minutes and the reaction mixture was slowly brought to room temperature. After 3 hours, the reaction was partitioned between ethyl acetate and 1 M HCl solution and washed with brine solution. The organic phase was collected and dried over $Na_2SO_4$, filtered and concentrated in vacuo to afford 8.17 g (99.6%) of 5-(tert-butyldiphenyl-silanyloxymethyl)-2,3,4-trifluoro-benzoic acid as a white, waxy solid.

Step c: To a suspension of 5-(tert-butylphenyl-silanyloxymethyl)-2,3,4-trifluoro-benzoic acid (8.17 g, 18.4 mmol) in freshly distilled THF (20 mL) was added a solution of tetrabutylammonium fluoride (1.0 M in THF, 40.0 mL, 40.0 mmol). After stirring at room temperature for 2 hours the reaction mixture was concentrated in vacuo and redissolved in ethyl acetate, transferred to a separatory funnel and washed 3 times with 1M HCl solution, 2 times with saturated brine solution. The organic layers were collected, dried over $Na_2SO_4$, filtered and concentrated in vacuo. To the resulting residue was added hexanes affording a white solid, which was washed several times with hexanes, collected and dried in vacuo affording 2,3,4-tifluoro-5-hydroxymethyl-benzoic acid (1.98 g, 52.2%).

Step d: To a refluxing suspension of trifluoro-5-hydroxymethyl-benzoic acid (1.90 g, 9.22 mmol) in acetone is added a solution of potassium permanganate (4.3 g, 27.7 mmol) in water (5 mL). After refluxing for 6 hours the reaction is allowed to cool and an aqueous solution of $NaHSO_3$ (5 mL, 1.0 M) and an aqueous solution of $H_2SO_4$ (5 mL, 1.0 M) is added which clears the reaction solution. This mixture is transferred to a separatory funnel and extracted several times with ethyl acetate. The organic layers are collected, dried over $Na_2SO_4$, filtered and concentrated in vacuo affording 4,5,6-trifluoro-isophthalic acid as a light yellow solid (1.03 g, 50.7%).

Step e: A suspension of 4,5,6-trifluoro-isophthalic acid (1.03 g, 4.68 mmol) in freshly distilled THF (20 mL) at –78° C. under nitrogen is treated with 2.0 equivalents of freshly prepared 1 M LiHMDS solution (HMDS, 2.07 mL, 9.83 mmol; n-butyllithium, 3.5 mL, 9.36 mmol) in THF. In a second flask is suspended 4-iodo-2-methylaniline (1.09 g, 4.68 mmol) in 20 mL of freshly distilled THF, cooled to –78° C. under nitrogen and treated with 2.0 equiv. of freshly prepared 1M LiHMDS solution (HMDS, 2.07 mL, 9.83 mmol; n-butyllithium, 3.5 mL, 9.36 mmol) in THF. After both solutions stirred for 30 minutes at –78° C., the benzoic acid solution was cannula transferred into the aniline solution and allowed to slowly warm to room temperature. After stirring for 4 hours, the reaction mixture was poured into 200 mL of a saturated HCl diethyl ether solution affording a white precipitate. The solid is filtered off and the remaining filtrate is collected and concentrated in vacuo affording 4,5-fluoro-6-(4-iodo-2-methyl-phenylamino)-isophthalic acid (1.55 g, 77%).

Step f: A suspension of 4,5-difluoro-6-(4-iodo-2-methyl-phenylamino)-isophthalic acid (1.1 g, 2.54 mmol), paraformaldehyde (5.0 g), and para-toluenesulfonic acid monohydrate (15.0 mg) in dichloromethane (250 mL) in a roundbottom flask attached with a Dean-Stark apparatus is allowed to reflux for 3 hours. The cooled solution is then concentrated and the residue is redissolved in methanol and paraformaldehyde is filtered off and filtrate is collected and concentrated in vacuo affording 7,8-difluoro-1-(4-iodo-2-methyl-phenyl)-4-oxo-1,4-dihydro-2H-benzo[d][1,3]oxazine-6-carboxylic acid as a red solid (0.80 g, 70.0%).

EXAMPLE 2

7,8-Difluoro-1-(4-iodo-2-methyl-phenyl)-4-oxo-1,4-dihydro-2H-benzo[d][1,3]oxazine-6-carboxylic acid methylamide

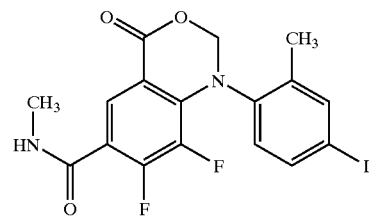

To a suspension of 7,8-difluoro-1-(4-iodo-2-methyl-phenyl)-4-oxo-1,4-dihydro-2H-benzo[d][1,3]oxazine-6-carboxylic acid (0.3 g, 0.67 mmol) in N,N-dimethylformamide (3 mL) is added trifluoroacetic acid pentafluorophenyl ester (0.127 mL, 0.74 mmol) and pyridine (0.60 mL, 0.74 mmol). After stirring for 4 hours the reaction mixture is diluted with ethyl acetate and washed 3 times with 1.0 M HCl solution, 3 times with 5% aqueous $NaHCO_3$ solution, 2 times with water and once with saturated brine solution. The organic layers were collected and dried over $Na_2SO_4$, filtered and concentrated in vacuo affording 7,8-difluoro-1-(4-iodo-2-methyl-phenyl)-4-oxo-1,4-dihydro-2H-benzo[d][1,3]oxazine-6-carboxylic acid pentafluorophenylester as a dark orange oil (0.34 g, 83.1%). To a suspension of 7,8-difluoro-1-(4-iodo-2-methyl-phenyl)-4-oxo-1,4-dihydro-2H-benzo[d][1,3]oxazine-6-carboxylic acid pentafluorophenylester (0.33 g, 0.54 mmol) in freshly distilled THF (10 mL) is added methylamine hydrochloride (0.037 g, 0.54 mmol) and N,N-diisopropylethylamine (0.019 mL, 1.08 mmol). After stirring for 17 hours, the reaction mixture was diluted with ethyl acetate and washed 2 times with water and 2 times with saturated brine solution. The organic layers were collected and dried over $Na_2SO_4$, filtered and concentrated in vacuo affording 7,8-difluoro-1-(4-iodo-2-methyl-phenyl)-4-oxo-1,4-dihydro-2H-benzo[d][1,3]oxazine-6-carboxylic acid methylamide as a yellow solid (0.19 g, 76.9%); mp 219–223° C.; $^1$NMR (400 MHz; DMSO-d6) 8.40 (s, 1H), 8.06 (d, 1H, J=6.8), 7.74 (s, 1H), 7.50 (d, 1H, J=8.4), 6.87 (d, 1H, J=8.0), 5.61 (s, 2H), 2.76 (d, 3H, J=4.4), 2.25 (s, 3H); MS(APCI)m+1=459; Anal.calcd/found for $C_{17}H_{13}F_2IN_2O_3$ C 45.00/45.39, H 3.01/3.16, N 6.05/5.88.

in vitro MEK assay: $IC_{50}$=6.6 $\mu$M

EXAMPLE 3

4,5-Difluoro-6-(-4-iodo-2-methyl-phenylamino)-N-methyl-isophthalamic acid

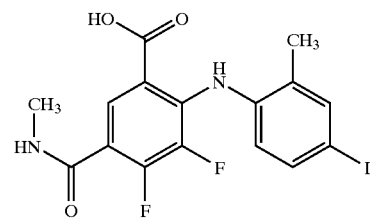

To a suspension of 7,8-difluoro-1-(4-iodo-2-methyl-phenyl)-4-oxo-1,4-dihydro-2H-benzo[d][1,3]oxazine-6-carboxylic acid methylamide in THF (10 mL) is added polymer bound glycerol, (0.33 g, 200–400 mesh) and 10 mL of 1.0 M HCl solution. After stirring for 48 hours at room temperature, the resin is filtered off and the filtrate is transferred to a separatory funnel and partitioned with ethyl acetate. The organics are washed twice with 1.0 M HCl, twice with saturated brine solution, collected, dried over $Na_2SO_4$, filtered and concentrated in vacuo affording 4,5-difluoro-6-(-4-iodo-2-methyl-phenylamino)-N-methyl-isophthalamic acid (0.11 g, 76.2%); mp 254–259° C.; $^1$H NMR (400 MHz; DMSO-d6) 9.31 (s, 1H), 8.19 (s, 1H), 8.07 (d, 1H, J=7.2), 7.56 (s, 1H), 6.69 (t, 1H, J=5.6), 2.74 (d, 3H, J=4.4), 2.20 (s, 3H); MS (APCI)m+1=447; Anal.calcd/found for $C_{16}H_{13}F_2IN_2O_3$, C 43.07/43.26, H 2.94/3.07. N 6.28/6.10. in vitro MEK assay: $IC_{50}$=2.4 μM

EXAMPLE 4

$N^1$-Cycloprolylmethoxy-4,5-difluoro-6-(4-iodo-2-methyl-phenylamino)-$N^3$-methyl-isophthalamide

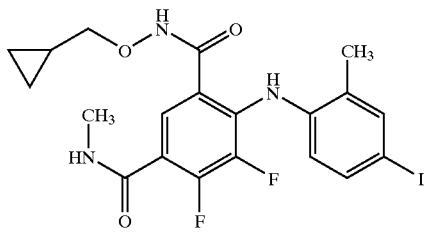

To a suspension of 4,5-difluoro-6-(-4-iodo-2-methyl-phenylamino)-N-methyl-isophthalamic acid (0.13 g, 0.29 mmol) in N,N-dimethylformamide (5 mL) is added trifluoroacetic acid pentafluorophenyl ester (0.055 mL, 0.32 mmol) and pyridine (0.03 mL, 0.32 mmol). After stirring for 17 hours the reaction mixture is diluted with ethyl acetate and transferred to a separatory funnel, washed twice with 1.0 M HCl, twice with 5% aqueous $NaHCO_3$ solution, 2 times with water and once with saturated brine solution. The organic layers were collected and dried over $Na_2SO_4$, filtered and concentrated in vacuo affording 4,5-difluoro-6-(4-iodo-2-methyl-phenylamino)-N-methyl-isophthalamic acid pentafluorophenyl ester (0.08g, 45.2%). To a suspension of 4,5-difluoro-6-(-4-iodo-2-methyl-phenylamino)-N-methyl-isophthalamic acid pentafluorophenyl ester (0.08 g, 0.13 mmol) in freshly distilled THF (3 mL) is added cyclopropylmethylamine hydrochloride (0.016 g, 0.13 mmol), and N,N-diisopropylethylamine (0.07 mL, 0.39 mmol). After stirring at room temperature for 17 hours the reaction mixture was partitioned between ethyl acetate and 1.0 M HCl solution. The organic layer was washed twice with water, twice with saturated brine solution, dried over $MgSO_4$, filtered and concentrated in vacuo. Purification was performed by silica column chromatography in 2:1 ethyl acetate:hexanes affording $N^1$-cyclopropylmethoxy-4,5-difluoro-6-(4-iodo-2-methyl-phenylamino)-$N^3$-methyl-isophthalamide (0.033, 42.8%); mp 198–202° C.; $^1$H NMR (400 MHz; DMSO-d6) 8.59 (s, 1H), 8.01 (s, 1H), 7.44 (d, 1H, J=5.2), 7.32 (s, 1H), 7.18 (d, 1H, J=7.6), 6.36 (m,1H), 3.34 (d, 2H, J=6.8), 2.56 (d, 3H, J=4.0), 1.99 (s, 3H), 0.82 (m, 1H), 0.27 (d, 2H, J=8.4), 0.00 (m, 2H); MS(APCI)m+1=516; Anal.calcd/found for $C_{20}H_{20}F_2IN_3O_3$ C 47.08/46.85, H 4.22/4.02 N 7.68/7.29.
in vitro MEK assay: $IC_{50}$=1.1 μM

EXAMPLE 5

7,8-Difluoro-1-(4-iodo-2-methyl-phenyl)-4-oxo-1,4-dihydro-2H-benzo[d][1,3]oxazine-6-carboxylic acid dimethylamide

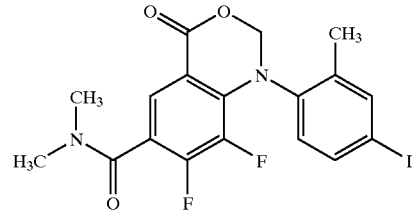

Prepared in the manner of Example 4
$^1$H NMR (400 MHz; CDCl$_3$) 7.96 (dd, 1H, J=2.2, 6.6), 7.65 (t, 1H, J=1.5), 7.48 (dd, 1H, J=1.7, 8.3), 6.70 (d, 1H, J=8.3), 5.37 (s, 2H), 3.11 (s, 3H), 2.96 (s, 3H), 2.3 (s, 3H); MS(APCI)m+1=473; Anal.calcd/found for $C_{18}F_{15}F_2IN_2O_3$ C 46.66/47.05, H 3.80/3.65, N 5.34/5.58.
in vitro MEK assay: $IC_{50}$=5.8 μM

EXAMPLE 6

$N^1$-Cyclopropylmethoxy-4,5-difluoro-6-(4-iodo-2-methyl-phenylamino)-$N^3$,$N^3$-dimethyl-isophthalamide (27)

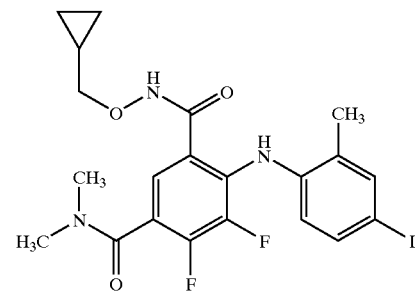

Prepared in the manner of Example 4
mp 78–80° C.; $^1$H NMR (400 MHz; DMSO-d$_6$) 8.52 (s, 1H), 7.32 (s, 1H), 7.15 (m, 1H), 6.39 (m, 1H), 3.35 (d, 2H, J=6.8), 2.79 (s, 3H), 2.72 (s, 3H), 2.00 (s, 3H), 0.93 (m, 1H), 0.27 (d, 2H, J=8.0), 0.00 (m, 2H); MS(APCI) m+1=530.
in vitro MEK assay: $IC_{50}$=4.3 μM

EXAMPLE 7

The following were prepared using parallel synthetic techniques in the following manner:

Step A:
  A solution of 7,8-difluoro-1-(4-iodo-2-methyl-phenyl)-4-oxo-1,4-dihydro-2H-benzo[d][1,3]oxazine-6-carboxylic acid pentafluorophenylester in a 2:1 mixture of THF to N,N-dimethylformamide (0.32M, 19.36 g) was prepared. In preweighed 2-dram glass vials was added the corresponding amine (0.35 mmol) and then the prepared 7,8-difluoro-1-(4-iodo-2-methyl-phenyl)-4-oxo-1,4-dihydro-2H-benzo[d][1,3]oxazine-6-carboxylic acid pentafluorophenylester solution (0.3 mmol). To each vial was added a morpholine polystyrene resin (0.2 g), capped with Teflon coated caps and placed on an orbital shaker for 24 hours. The individual reactions were then charged with polyamine polystyrene resin (0.2 g) and isocyanate polystyrene resin (0.1 g) and dichloromethane (2 mL) and allowed to shake for another 17 hours. The reactions were filtered and concentrated in vacuo to afford the corresponding 7,8-difluoro-1-(4-iodo-2-methyl-phenyl)-4-oxo-1,4-dihydro-2H-benzo[d][1,3]oxazine-6-carboxylic acid amides. LC/MS was performed on a CPI 120SE (C18) column (4.6×50 mm, 5 μm).

EXAMPLE 8

7,8-Difluoro-6-((R)-3-hydroxy-pyrrolidine-1-carbonyl)-1-(4-iodo-2-methyl-phenyl)-1,2-dihydro-3,1-benzoxazin-4-one

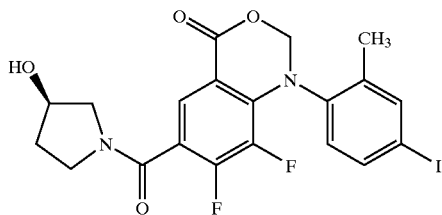

$C_{20}H_{17}F_2IN_2O_4$, MS (APCI)m+1=515
in vitro MEK assay: 34% inhibition @ 1 μM

EXAMPLE 9

7,8-Difluoro-1-(4-iodo-2-methyl-phenyl)-6-((S)-2-methoxymethyl-pyrrolidine-1-carbonyl)-1,2-dihydro-3,1-benzoxazin-4-one

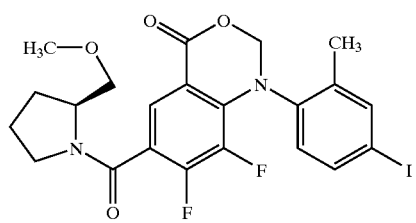

$C_{22}H_{21}F_2IN_2O_4$, MS (APCI)m+1=543
in vitro MEK assay: 93% inhibition @ 1 μM

EXAMPLE 10

7,8-Difluoro-1-(4-iodo-2-methyl-phenyl)-4-oxo-1,4-dihydro-2H-3,1-benzoxazine-6-carboxylic acid (2-piperidin-1-yl-ethyl)-amide

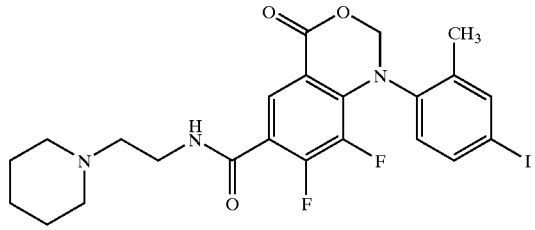

$C_{23}H_{24}F_2IN_3O_3$, MS (APCI)m+1=556
in vitro MEK assay: 44% inhibition @ 1 μM

EXAMPLE 11

7,8-Difluoro-1-(4-iodo-2-methyl-phenyl)-4-oxo-1,4-dihydro-2H-3,1-benzoxazine-6-carboxylic acid (2-pyrrolidin-1-yl-ethyl)-amide

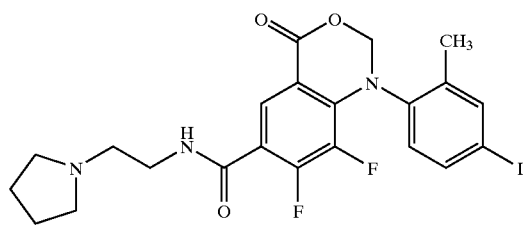

$C_{22}H_{22}F_2IN_3O_3$, MS (APCI)m+1+542
in vitro MEK assay: 33% inhibition @ 1 μM

EXAMPLE 12

7,8-Difluoro-1-(4-iodo-2-methyl-phenyl)-4-oxo-1,4-dihydro-2H-3,1-benzoxazine-6-carboxylic acid [3-(2-oxo-pyrrolidin-1-y)-propyl]-amide

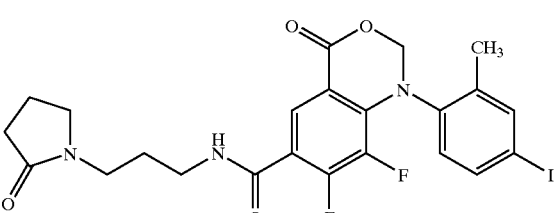

$C_{23}H_{22}F_2IN_3O_4$, MS (APCI)m+1=570
in vitro MEK assay: 21% inhibition @ 1 μM

EXAMPLE 13

7,8-Difluoro-1-(4-iodo-2-methyl-phenyl)-4-oxo-1,4-dihydro-2H-3,1-benzoxazine-6-carboxylic acid (1-hydroxy-cyclohexylmethyl)-amide

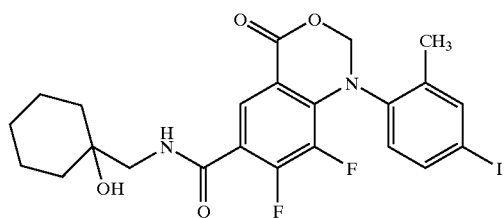

$C_{23}H_{23}F_2IN_2O_4$, MS (APCI)m+1=557
in vitro MEK assay: 23% inhibition @ 1 μM

EXAMPLE 14

7,8-Difluoro-1-(4-iodo-2-methyl-phenyl)-4-oxo-1,4-dihydro-2H-3,1-benzoxazine-6-carboxylic acid (pyridin-2-ylmethyl)-amide $C_{27}H_{24}F_2IN_3O_3$, MS (APCI)m+1=604

EXAMPLE 15

4-[7,8-Difluoro-1-(4-iodo-2-methyl-phenyl)-4-oxo-1,4-dihydro-2H-3,1-benzoxazine-6-carbonyl]-piperazine-1-carbaldehyde

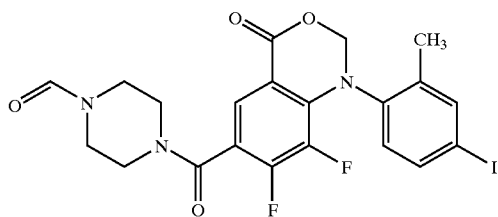

$C_{21}H_{18}F_2IN_3O_4$, MS (APCI)m+1=542
in vitro MEK assay: 13% inhibition @ 1 μM

EXAMPLE 16

7,8-Difluoro-1-(4-iodo-2-methyl-phenyl)-oxo-1,4-dihydro-2H-3,1-benzoxazine-6-carboxylic acid methyl-(1-methyl-piperidin-4-ylamide

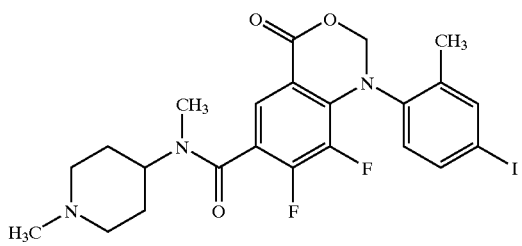

$C_{23}H_{24}F_2IN_3O_3$, MS (APCI)m+1=556
in vitro MEK assay: 0% inhibition @ 1 μM

EXAMPLE 17

7,8-Difluoro-1-(4-iodo-2-methyl-phenyl)-6-(4-methyl-piperazine-1-carbonyl-1,2-dihydro-3,1-benzoxazin-4-one

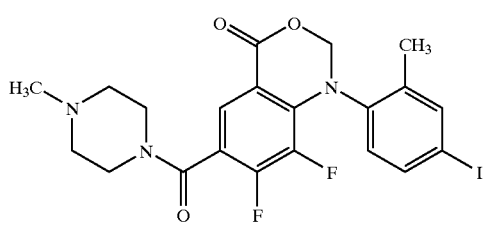

$C_{21}H_{20}F_2IN_3O_3$, MS (APCI)m+1=528
in vitro MEK assay: 78% inhibition @ 1 μM

EXAMPLE 18

7,8-Difluoro-1-(4-iodo-2-methyl-phenyl)-4-1,4-dihydro-2H-3,1-benzoxazine-6-carboxylic acid [2-(2-hydroxy-ethoxy)-ethyl]-amide

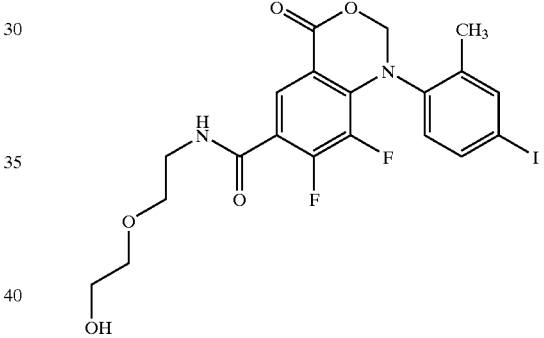

$C_{20}H_{19}F_2IN_2O_5$, MS (APCI)m+1=533
in vitro MEK assay: 43% inhibition @ 1 μM

EXAMPLE 19

7,8-Difluoro-1-(4-iodo-2-methyl-phenyl)-4-oxo-1,4-dihydro-2H-3,1-benzoxazine-6-carboxylic acid [2-(1-methyl-pyrrolidin-2-yl)ethyl]-amide

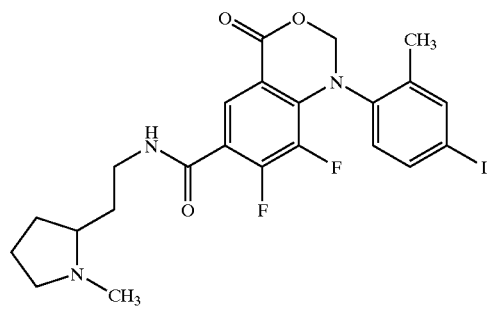

$C_{23}H_{24}F_2IN_3O_3$, MS (APCI)m+1=556
in vitro MEK assay: 28% inhibition @ 1 μM

EXAMPLE 20

7,8-Difluoro-1-(4-iodo-2-methyl-phenyl)-4-oxo-1,4-dihydro-2H-3,1-benzoxazine-6-carboxylic acid (2-hydroxy-ethyl)-methyl-amide

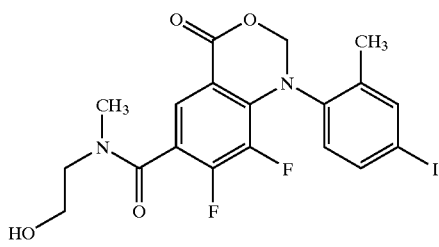

$C_{19}H_{17}F_2IN_2O_4$, MS (APCI)m+1=503
in vitro MEK assay: 41% inhibition @ 1 μM

EXAMPLE 21

7,8-Difluoro-1-(4-iodo-2-methyl-phenyl)-oxo-1,4-dihydro-2H-3,1-benzoxazine-6-carboxylic acid 1,3,4-thiadiazol-2-ylamide

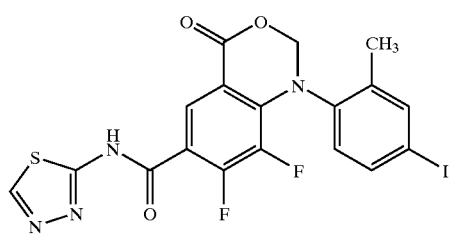

$C_{18}H_{11}F_2IN_4O_3S$, MS (APCI)m+1=529
in vitro MEK assay: 31% inhibition @ 1 μM

EXAMPLE 22

7,8-Difluoro-1-(4-iodo-2-methyl-phenyl)-4-oxo-1,4-dihydro-2H-3,1-benzoxazine-6-carboxylic acid (2-methoxy-1-methyl-ethyl)-amide

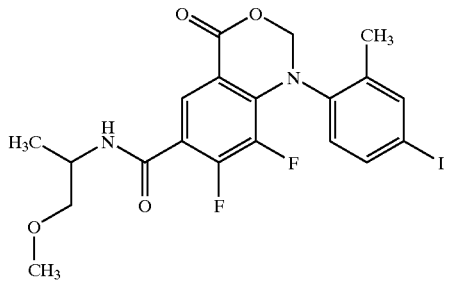

$C_{20}H_{19}F_2IN_2O_4$, MS (APCI)m+1=517
in vitro MEK assay: 46% inhibition @ 1 μM

EXAMPLE 23

7,8-Difluoro-1-(4-iodo-2-methyl-phenyl)-4-oxo-1,4-dihydro-2H-3,1-benzoxazine-6-carboxylic acid (4-methyl-benzothiazol-2-yl)-amide

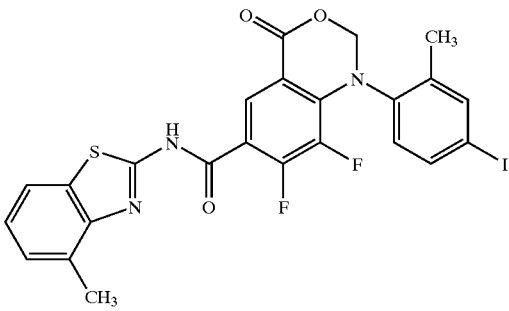

$C_{24}H_{16}F_2IN_3O_3S$, MS (APCI)m+1=592
in vitro MEK assay: 26% inhibition @ 1 μM

EXAMPLE 24

,8-Difluoro-1-(4-iodo-2-methyl-phenyl)-4-oxo-1,4dihydro-2H-3,1-benzoxazine-6-carboxylic acid (4-methyl-thiazol-2-yl)-amide

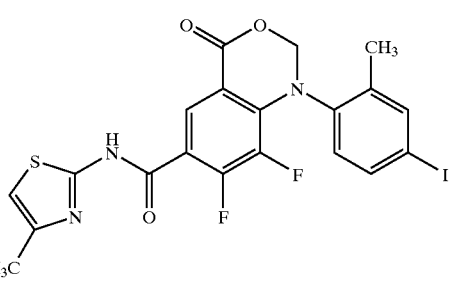

$C_{20}H_{14}F_2IN_3O_3S$, MS (APCI)m+1=542
in vitro MEK assay: 20% inhibition @ 1 μM

EXAMPLE 25

7,8-Difluoro-1-(4-iodo-2-methyl-phenyl)-4-oxo-1,4-dihydro-2H-3,1-benzoxazine-6-carboxylic acid (5-ethylsulfanyl-1,3,4-thiadiazol-2-yl)-amide

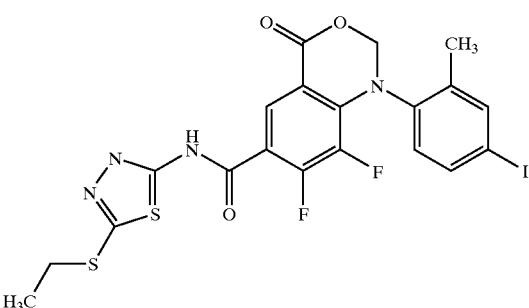

$C_{20}H_{15}F_2IN_4O_3S_2$, MS (APCI)m+1=589
in vitro MEK assay: 5% inhibition @ 1 μM

EXAMPLE 26

7,8-Difluoro-1-(4-iodo-2-methyl-phenyl)-4-oxo-1,4-dihydro-2H-3,1-benzoxazine-6-carboxylic acid (5-ethyl-1,3,4-thiadiazol-2-yl)-amide

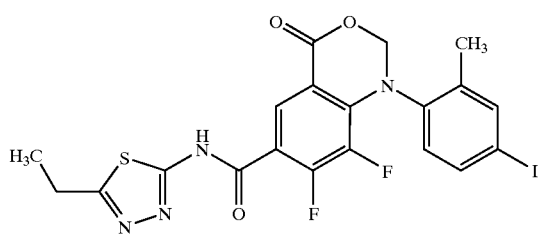

$C_{20}H_{15}F_2IN_4O_3S$, MS (APCI)m+1=557
in vitro MEK assay: 20% inhibition @ 1 μM

EXAMPLE 27

7,8-Difluoro-1-(4-iodo-2-methyl-phenyl)-4-oxo-1,4-dihydro-2H-3,1-benzoxazine-6-carboxylic acid (5-mercapto-1,3,4-thiadiazol-2-yl)-amide

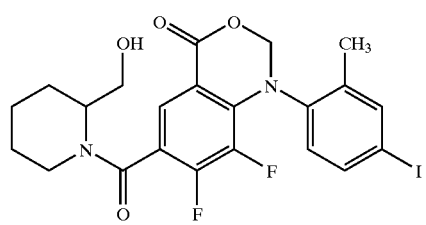

$C_{18}H_{11}F_2IN_4O_3S_2$, MS (APCI)m+1=561
in vitro MEK assay: 27% inhibition @ 1 μM

EXAMPLE 28

7,8-Difluoro-1-(4-iodo-2-methyl-phenyl)-4-oxo-1,4-dihydro-2H-3,1-benzoxazine-6-carboxylic acid (6-ethoxy-benzothiazol-2-yl)-amide

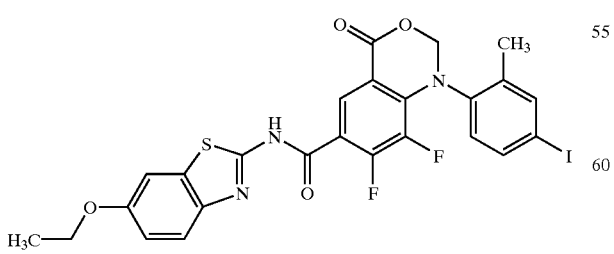

$C_{25}H_{18}F_2IN_3O_4S$, MS (APCI)m+1=622
in vitro MEK assay: 9% inhibition @ 1 μM

EXAMPLE 29

7,8-Difluoro-1-(4-iodo-2-methyl-phenyl)-4-oxo-1,4-dihydro-2H-3,1-benzoxazine-6-carboxylic acid benzothiazol-2-ylamide

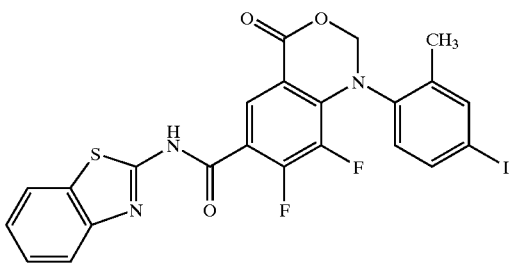

$C_{23}H_{14}F_2IN_3O_3S$, MS (APCI)m+1=578
in vitro MEK assay: 21% inhibition @ 1 μM

EXAMPLE 30

7,8-Difluoro-1-(4-iodo-2-methyl-phenyl)-4-oxo-1,4-dihydro-2H-3,1-benzoxazine-6-carboxylic acid [2-(2-hydroxy-ethyl)-phenyl]-amide

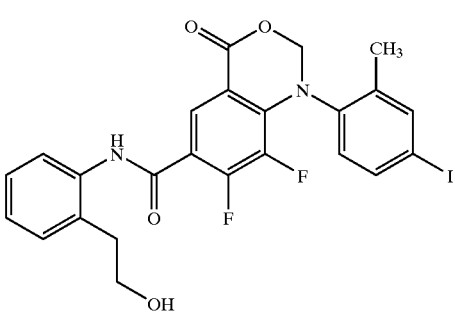

$C_{24}H_{19}F_2IN_2O_4$, MS (APCI)m+1=565
in vitro MEK assay: 55% inhibition @ 1 μM

EXAMPLE 31

7,8-Difluoro-1-(4-iodo-2-methyl-phenul)-4-oxo-1,4-dihydro-2H-3,1-benzoxazine-6-carboxylic acid thiazol-2-ylamide

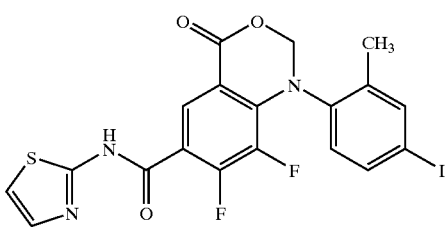

$C_{19}H_{12}F_2IN_3O_3S$, MS (APCI)m+1=528
in vitro MEK assay: 32% inhibition @ 1 μM

EXAMPLE 32

7,8-Difluoro-6-[2-(2-hydroxy-ethyl)-piperidine-1-carbonyl]-1-(4-iodo-2-methyl-phenyl)-1,2-dihydro-3,1-benzoxazin-4-one

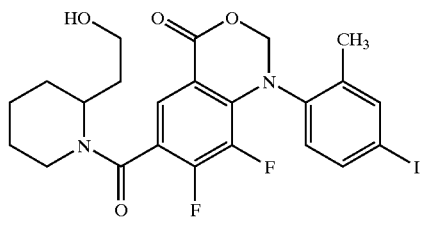

$C_{23}H_{23}F_2IN_2O_4$, MS (APCI)m+1=557
in vitro MEK assay: 76% inhibition @ 1 μM

EXAMPLE 33

7,8-Difluoro-6-(2-hydroxymethyl-piperidine-1-carbonyl)-1-(4-iodo-2-methyl-phenyl)-1,2-dihydro-3,1-benzoxazin-4-one

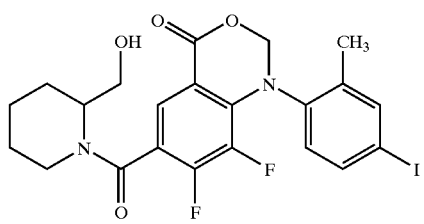

$C_{22}H_{21}F_2IN_2O_4$, MS (APCI)m+1=543
in vitro MEK assay: 79% inhibition @ 1 μM

EXAMPLE 34

3-{[7,8-Difluoro-1-(4-iodo-2-methyl-phenyl)-4-oxo-1,4-dihydro-2H-3,1-benzoxazine-6-carbonyl]-amino}-1H-pyrazole-4-carboxylic acid ethyl ester

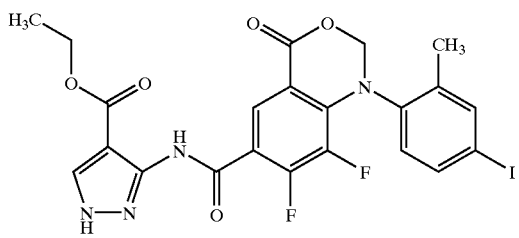

$C_{22}H_{17}F_2IN_4O_5$, MS (APCI)m+1=583
in vitro MEK assay: 72% inhibition @ 1 μM

EXAMPLE 35

7,8-Difluoro-1-(4-iodo-2-methyl-phenyl)-4-oxo-1,4-dihydro-2H-3,1-benzoxazine-6-carboxylic acid (5-methylsulfanyl-1H-1,2,4-triazol-3-yl)-amide

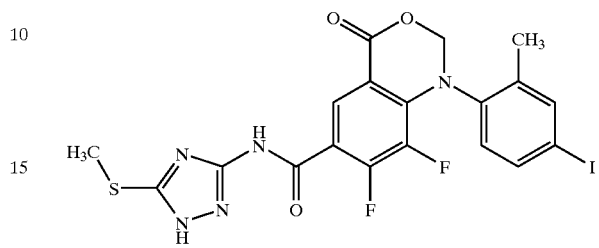

$C_{19}H_{14}F_2IN_5O_3S$, MS (APCI)m+1=558
in vitro MEK assay: 76% inhibition @ 1 μM

EXAMPLE 36

7,8-Difluoro-1-(4-iodo-2-methyl-phenyl)-4-oxo-1,4-dihydro-2H-3,1-benzoxazine-6-carboxylic acid (1H-pyrazol-3-yl)-amide

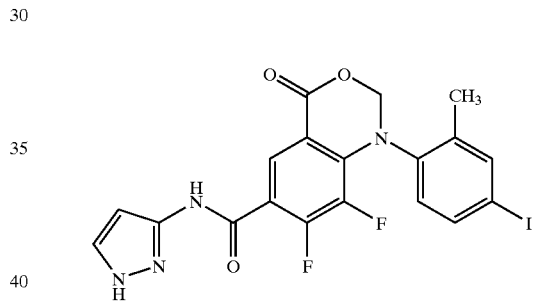

$C_{19}H_{13}F_2IN_4O_3$, MS (APCI)m+1=511
in vitro MEK assay: 60% inhibition @ 1 μM

EXAMPLE 37

7,8-Difluoro-1-(4-iodo-2-methyl-phenyl)-4-oxo-1,4-dihydro-2H-3,1-benzoxazine-6-carboxylic acid pyridin-3-ylamide

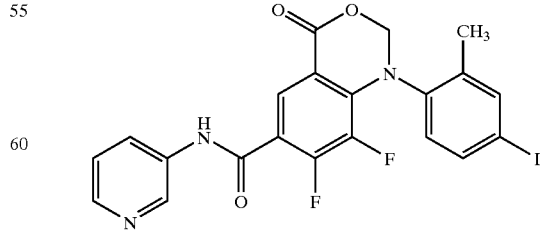

$C_{21}H_{14}F_2IN_3O_3$, MS (APCI)m+1=522
in vitro MEK assay: 20% inhibition @ 1 μM

EXAMPLE 38

7,8-Difluoro-6-(3-hydroxy-piperidine-1-carbonyl)-1-(4-iodo-2-methyl-phenyl)-1,2-dihydro-3,1-benzoxazin-4-one

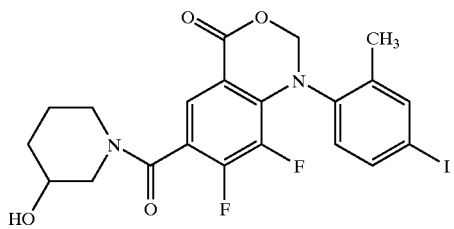

$C_{21}H_{19}F_2IN_2O_4$, MS (APCI)m+1=529
in vitro MEK assay: 48% inhibition @ 1 μM

EXAMPLE 39

7,8-Difluoro-6-(3-hydroxymethyl-piperidine-1-carbonyl)-1-(4-iodo-2-methyl-phenyl)-1,2-dihydro-3,1-benzoxazin-4-one

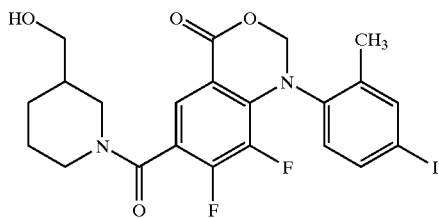

$C_{22}H_{21}F_2IN_2O_4$, MS (APCI)m+1=543
in vitro MEK assay: 71% inhibition @ 1 μM

EXAMPLE 40

7,8-Difluoro-6-(3-hydroxy-pyrrolidine-1-carbonyl)-1-(4-iodo-2-methyl-phenyl)-1,2-dihydro-3,1-benzoxazin-4-one

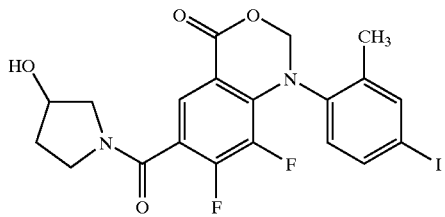

$C_{20}H_{17}F_2IN_2O_4$, MS (APCI)m+1=515
in vitro MEK assay: 42% inhibition @ 1 μM

EXAMPLE 41

7,8-Difluoro-1-(4-iodo-2-methyl-phenyl-6-(4-pyrrolidin-1-yl-piperidine-1-carbonyl)-1,2-dihydro-3,1-benzoxazin-4-one

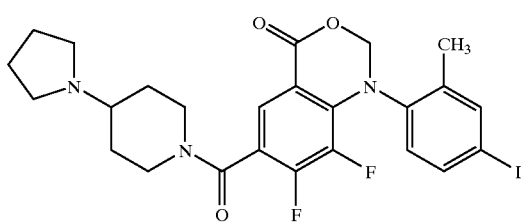

$C_{25}H_{26}F_2IN_3O_3$, MS (APCI)m+1=582
in vitro MEK assay: 7% inhibition @ 1 μM

EXAMPLE 42

7,8-Difluoro-1-(4-iodo-2-methyl-phenyl)-4-oxo-1,4-dihydro-2H-3,1-benzoxazine-6-carboxylic acid (2-morpholin-4yl-ethyl)-amide

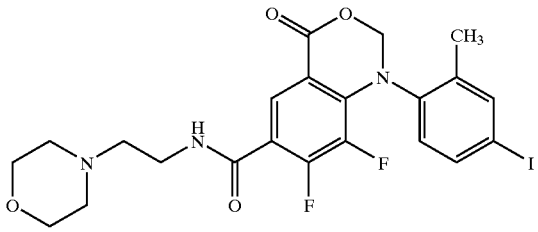

$C_{22}H_{22}F_2IN_3O_4$, MS (APCI)m+1=558
in vitro MEK assay: 15% inhibition @ 1 μM

EXAMPLE 43

7,8-Difluoro-6-(4-hydroxy-piperidine-1-carbonyl)1-(4-iodo-2-methyl-phenyl)-1,2-dihydro-3,1-benzoxazin-4-one

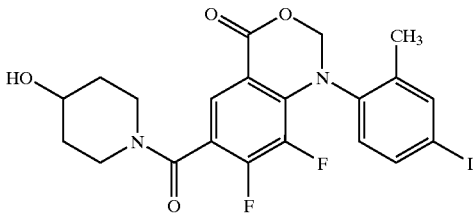

$C_{21}H_{19}F_2IN_2O_4$, MS (APCI)m+1=529
in vitro MEK assay: 52% inhibition @ 1 μM

EXAMPLE 44

7,8-Difluoro-6-[4-(2-hydroxy-ethyl)-piperidine-1-carbonyl]-1-(4-iodo-2-methyl-phenyl)-1,2-dihydro-3,1-benzoxazin-4-one

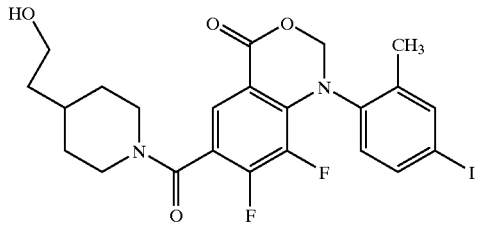

$C_{23}H_{23}F_2IN_2O_4$, MS (APCI)m+1=557
in vitro MEK assay: 69% inhibition @ 1 μM

EXAMPLE 45

7,8-Difluoro-1-(4-iodo-2-methyl-phenyl4-oxo-1,4-dihydro-2H-3,1-benzoxazine-6-carboxylic acid (6-chloro-pyridin-3-yl)-amide

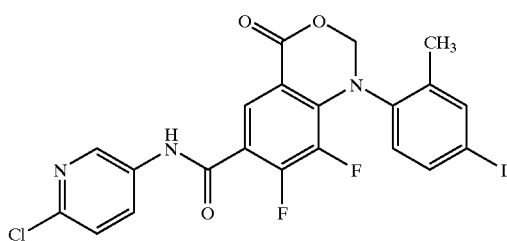

$C_{21}H_{13}ClF_2IN_3O_3$, MS (APCI)m+1=556
in vitro MEK assay: 62% inhibition @ 1 μM

EXAMPLE 46

7,8-Difluoro-1-(4-iodo-2-methyl-phenyl)-4-oxo-1,4-dihydro-2H-3,1-benzoxazine-6-carboxylic acid (6-methoxy-pyridin-3-yl)amide

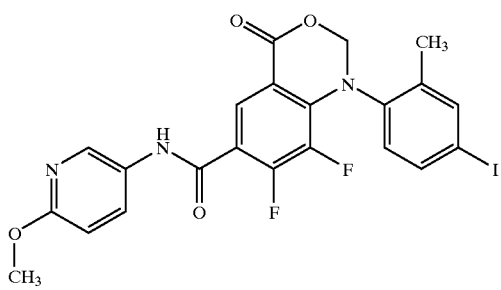

$C_{22}H_{16}F_2IN_3O_4$, MS (APCI)m+1=552
in vitro MEK assay: 43% inhibition @ 1 μM

EXAMPLE 47

7,8-Difluoro-1-(4-iodo-2-methyl-2-phenyl)-4-oxo-1,4-dihydro-2H-3,1-benzoxazine-6-carboxylic acid [2-(5-methoxy-1H-indol-3-yl)ethyl]-amide

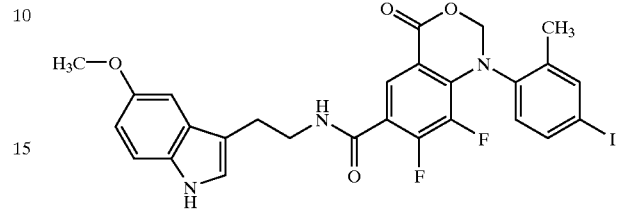

$C_{27}H22F_2IN_3O_4$, MS (APCI)m+1=618
in vitro MEK assay: 0% inhibition @ 1 μM

EXAMPLE 48

7,8-Difluoro-1-(4-iodo-2-methyl-phenyl)-4-oxo-1,4-dihydro-2H-3,1-benzoxazine-6-carboxylic acid [2-(6-methoxy-1H-indol-3-yl)-ethyl]-amide

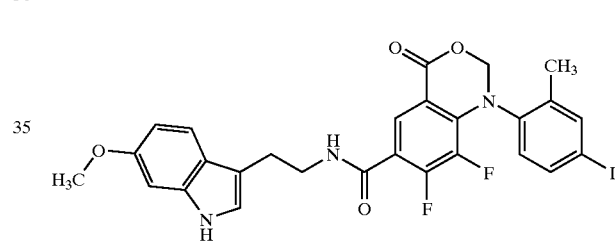

$C_{27}H22F_2IN_3O_4$, MS (APCI)m+1=618
in vitro MEK assay: 12% inhibition @ 1 μM

EXAMPLE 49

7,8-Difluoro-1-(4-iodo-2-methyl-phenyl)-4-oxo-1,4-dihydro-2H-3,1-benzoxazine-6-carboxylic acid bis-(2-hydroxy-ethyl)-amide

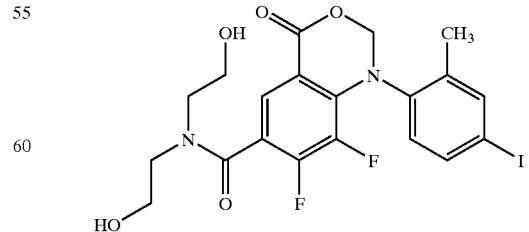

$C_{20}H_{19}F_2IN_2O_5$, MS (APCI)m+1=533
in vitro MEK assay: 50% inhibition @ 1 μM

EXAMPLE 50

7,8-Difluoro-1-(4-iodo-2-methyl-phenyl)4-oxo-1,4-dihydro-2H-3,1-benzoxazine-6-carboxylic acid [2-(1H-imidazol4-yl)-ethyl]-amide

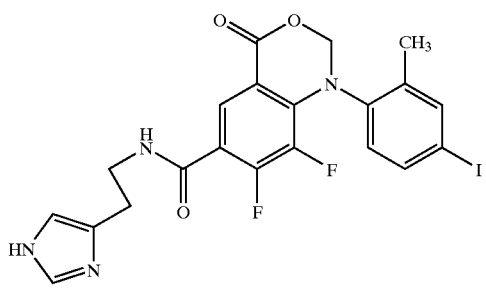

$C_{21}H_{17}F_2IN_4O_3$, MS (APCI)m+1=539
in vitro MEK assay: 44% inhibition @ 1 μM

EXAMPLE 51

7,8-Difluoro-1-(4-iodo-2-methyl-phenyl)-6-(morpholine-4-carbonyl)-1,2-dihydro-3,1-benzoxazin-4-one

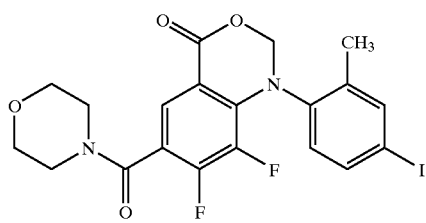

$C_{20}H_{17}F_2IN_2O_4$, MS (APCI)m+1=515
in vitro MEK assay: 72% inhibition @ 1 μM

EXAMPLE 52

7,8-Difluoro-1-(4-iodo-2-methyl-phenyl)-4-oxo-1,4-dihydro-2H-3,1-benzoxazine-6-carboxylic acid (3-imidazol-1-yl-propyl)amide

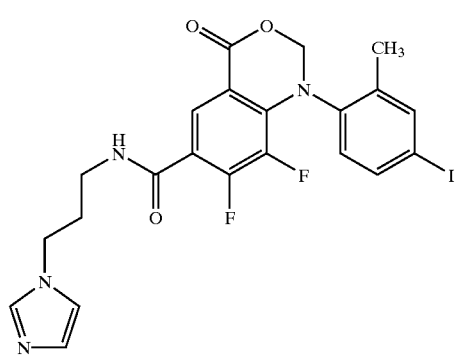

$C_{22}H_{19}F_2IN_4O_3$, MS (APCI)m+1 =553
in vitro MEK assay: 35% inhibition @ 1 μM

EXAMPLE 53

7,8-Difluoro-1-(4-iodo-2-methyl-phenyl)-4-oxo-1,4-dihydro-2H-3,1-benzoxazine-6-carboxylic acid (4-dimethylamino-phenyl)amide

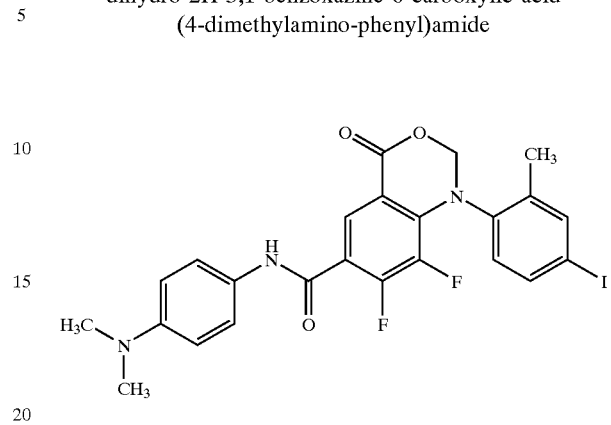

$C_{24}H_{20}F_2IN_3O_3$, MS (APCI)m+1=564
in vitro MEK assay: 61% inhibition @ 1 μM

EXAMPLE 54

6-(4-Ethyl-piperazine-1-carbonyl)-7,8-difluoro-1-(4-iodo-2-methyl-phenyl)-1,2-dihydro-3,1-benzoxazin-4-one

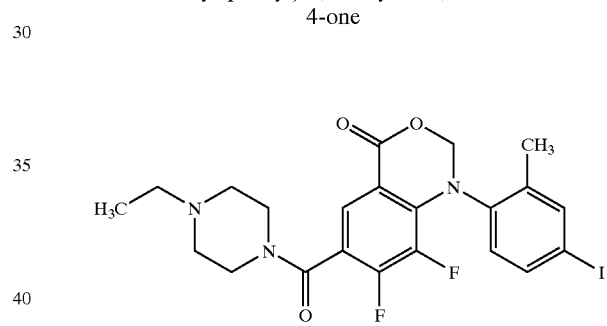

$C_{22}H_{22}F_2IN_3O_3$, MS (APCI)m+1=542
in vitro MEK assay: 56% inhibition @ 1 μM

EXAMPLE 55

7,8-Difluoro-1-(4-iodo-2-methyl-phenyl)-4-oxo-1,4-dihydro-2H-3,1-benzoxazine-6-carboxylic acid [2-(1H-indol-3-yl)ethyl ]-methyl-amide

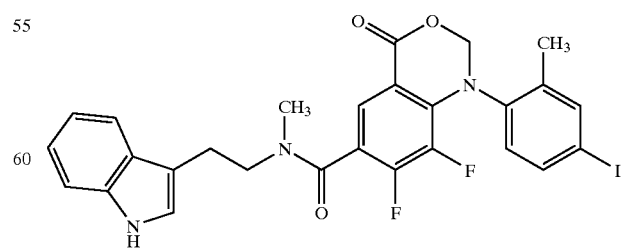

$C_{27}H_{22}F_2IN_3O_3$, MS (APCI)m+1=602
in vitro MEK assay: 41% inhibition @ 1 μM

EXAMPLE 56

7,8-Difluoro-1-(4-iodo-2-methyl-phenyl)-6-(piperazine-1-carbonyl)-1,2-dihydro-3,1-benzoxazin-4-one

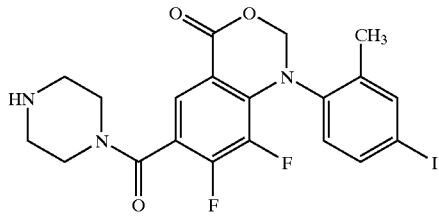

$C_{20}H_{18}F_2IN_3O_3$, MS (APCI)m+1=514
in vitro MEK assay: 1% inhibition @ 1 μM

EXAMPLE 57

7,8-Difluoro-1-(4-iodo-2-methyl-phenyl)4-oxo-1,4-dihydro-2H-3,1-benzoxazine-6-carboxylic acid (tetrahydro-furan-2-ylmethyl)-amide

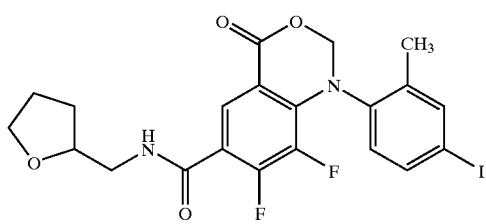

$C_{21}H_{19}F_2IN_2O_4$, MS (APCI)m+1=529
in vitro MEK assay: 35% inhibition @ 1 μM

EXAMPLE 58

7,8-Difluoro-1-(4-iodo-2-methyl-phenyl)-6-(thiazolidine-3-carbonyl)-1,2-dihydro-3,1-benzoxzin-4-one

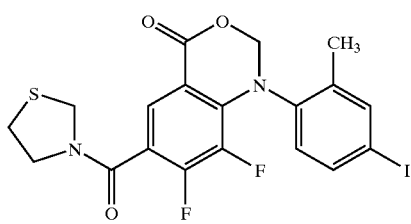

$C_{19}H_{15}F_2IN_2O_3S$, MS (APCI)m+1=517
in vitro MEK assay: 76% inhibition @ 1 μM

EXAMPLE 59

7,8-Difluoro-1-(4-iodo-2-methyl-phenyl)-6-(thiomorpholine-4-carbonyl)-1,2-dihydro-3,1-benzoxzin-4-one

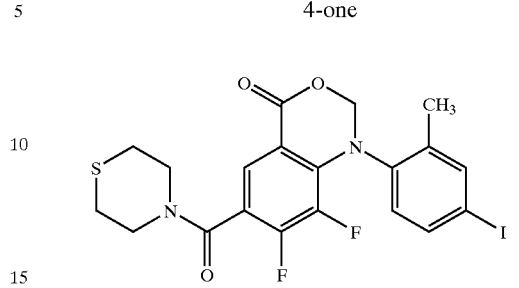

$C_{20}H_{17}F_2IN_2O_3S$, MS (APCI)m+1=531
in vitro MEK assay: 75% inhibition @ 1 μM

EXAMPLE 60

7,8-difluoro-1-(4-iodo-2-methyl-phenyl)-4-oxo-1,4-dihydro-2H-3,1-benzoxazine-6-carboxylic acid ((S)-2-hydroxy-cyclohexyl)-amide

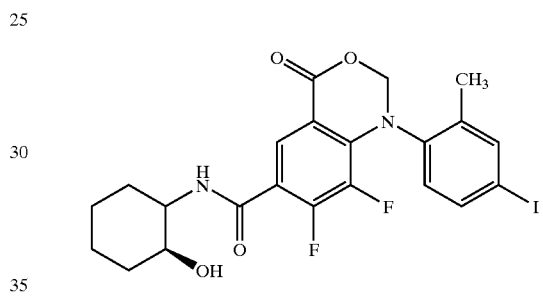

$C_{22}H_{21}F_2IN_2O_4$, MS (APCI)m+1=543
in vitro MEK assay: 30% inhibition @ 1 μM Step B:
To each of the 2 dram vials containing the 7,8-Difluoro-1-(4-iodo-2-methyl-phenyl)-4-oxo-1,4-dihydro-2H-benzo[d][1,3]oxazine-6-carboxylic acid amides was added THF (1 mL) and aqueous HCl (1.0 M, 1 mL) and glycerol polystyrene resin (0.2 g), capped with Teflon coated caps and allowed to shake on an orbital shaker at 50° C. for 5 days. The reactions were filtered and washed with ethyl acetate (1.5 mL) and concentrated in vacuo. HPLC purification was performed in acetonitrile/water (0.05%TFA) on a YM C30 (C18) column (100 mm ODS-A) to afford the corresponding isophthalamic acids. LC/MS was performed on a CPI 120SE (C18) column (4.6×50 mm, 5 μm).

EXAMPLE 61

3,4-Difluoro-5-[1-((R)-3-hydroxy-pyrrolidin-1-yl)-methanoyl]-2-(4-iodo-2-methyl-phenylamino)-benzoic acid

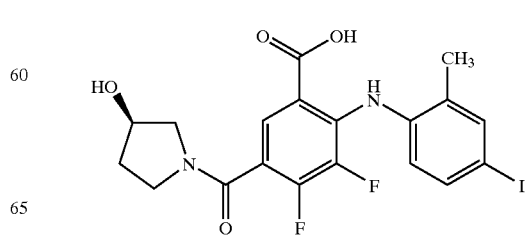

$C_{19}H_{17}F_2IN_2O_4$, MS (APCI)m+1=503
in vitro MEK assay: 75% inhibition @ 1 μM

EXAMPLE 62

4,5-Difluoro-6-(4-iodo-2-methyl-phenylamino)-N-[3-(2-oxo-pyrrolidin-1-yl)-propyl]-isophthalamic acid

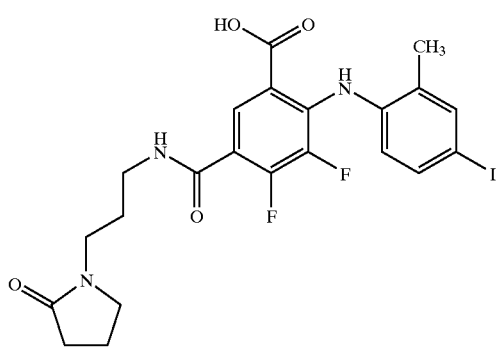

$C_{22}H_{22}F_2IN_3O_4$, MS (APCI)m+1=558
in vitro MEK assay: 78% inhibition @ 1 μM

EXAMPLE 63

4,5-Difluoro-6-(4-iodo-2-methyl-phenylamino)-N-(1-methyl-piperidin-4-yl)-isophthalamic acid

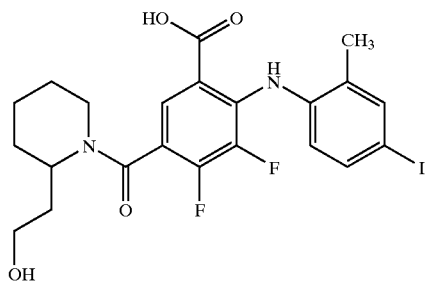

$C_{22}H_{24}F_2IN_3O_3$, MS (APCI)m+1=544
in vitro MEK assay: 0% inhibition @ 1 μM

EXAMPLE 64

3,4-Difluoro-2-(4-iodo-2-methyl-phenylamino)-5-[1-(4-methyl-piperazin-1-yl)-methanoyl]-benzoic acid

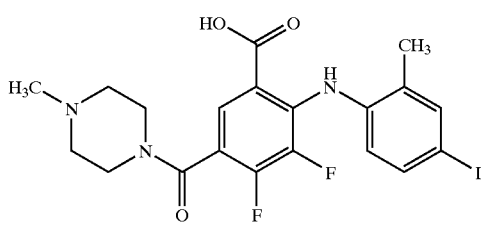

$C_{20}H_{20}F_2IN_3O_3$, MS (APCI)m+1=516
in vitro MEK assay: 57% inhibition @ 1 μM

EXAMPLE 65

4,5-Difluoro-N-[2-(2-hydroxy-ethoxy)-ethyl]-6-(4-iodo-2-methyl-phenylamino)-isophthalamic acid

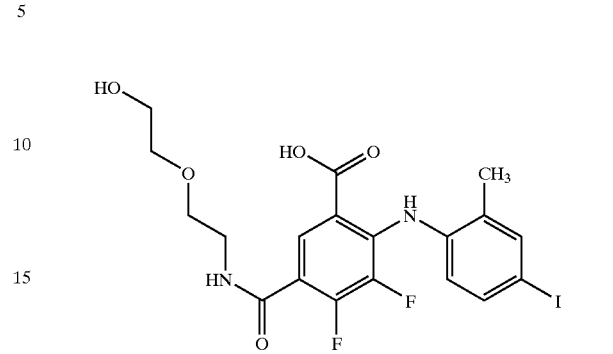

$C_{19}H_{19}F_2IN_2O_5$, MS (APCI)m+1=521
in vitro MEK assay: 63% inhibition @ 1 μM p0 in vitro MEK assay: IC$_{50}$=1.38 μM

EXAMPLE 66

4,5-Difluoro-6-(4-iodo-2-methyl-phenylamino)-N-[2-(1-methyl-pyrrolidin-2-yl)-ethyl]-isophthalamic acid

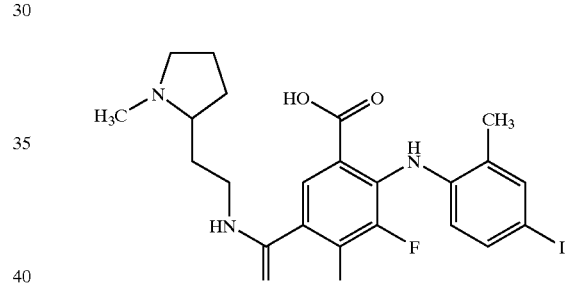

$C_{22}H_{24}F_2IN_2O_3$, MS (APCI)m+1=544
in vitro MEK assay: 14% inhibition @ 1 μM

EXAMPLE 67

4,5-Difluoro-6-(4-iodo-2-methyl-phenylamino)-N-(2-pyridin-2-yl-ethyl)-isophthalamic acid

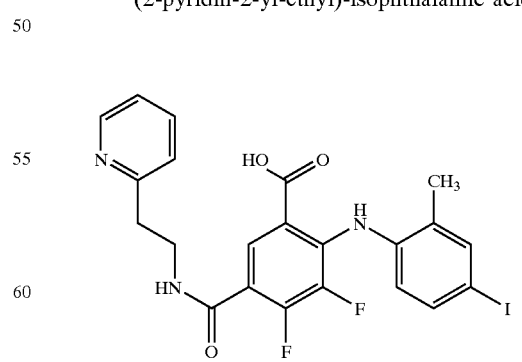

$C_{22}H_{18}F_2IN_3O_3$, MS (APCI)m+1=538
in vitro MEK assay: 81% inhibition @ 1 μM
in vitro MEK assay: IC$_{50}$=3.3 μM

EXAMPLE 68

N-Butyl-4,5-difluoro-6-(4-iodo-2-methyl-phenylamino)-N-(2-mercapto-ethyl)-isophthalamic acid

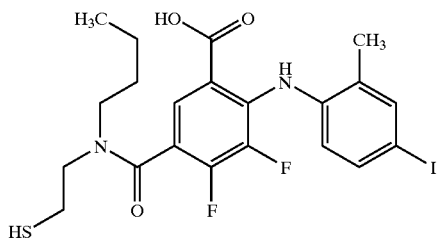

$C_{21}H_{23}F_2IN_2O_3S$, MS (APCI)m+1=549
in vitro MEK assay: 24% inhibition @ 1 μM

EXAMPLE 69

3,4-Difluoro-5-{1-[2-(2-hydroxy-ethyl)-piperidin-1-yl]-methanoyl}-2-(4-iodo-2-methyl-phenylamino)-benzoic acid

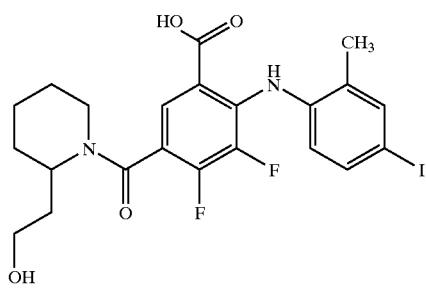

$C_{22}H_{23}F_2IN_2O_4$, MS (APCI)m+1=545
in vitro MEK assay: 78% inhibition @ 1 μM
in vitro MEK assay: $IC_{50}$=2.2 μM

EXAMPLE 70

3,4-Difluoro-5-[1-(2-hydroxymethyl-piperidin-1-yl)-methanoyl]-2-(4-iodo-2-methyl-phenylamino)-benzoic acid

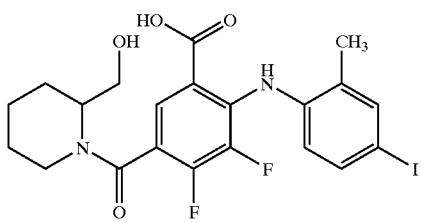

$C_{21}H_{21}F_2IN_2O_4$, MS (APCI)m+1=531
in vitro MEK assay: 49% inhibition @ 1 μM

EXAMPLE 71

4,5-Difluoro-6-(4-iodo-2-methyl-phenylamino)-N-pyridin-3-ylmethyl-isophthalamic acid

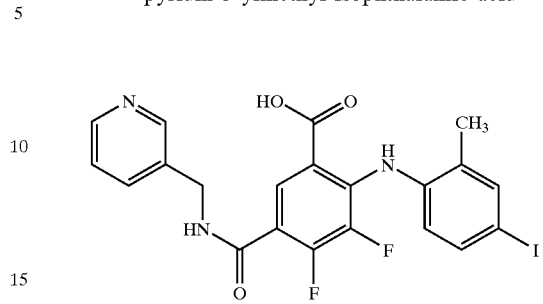

$C_{21}H_{16}F_2IN_3O_3$, MS (APCI)m+1=524
in vitro MEK assay: 86% inhibition @ 1 μM
in vitro MEK assay: $IC_{50}$=1.45 μM

EXAMPLE 72

N-(2,3-Dihydro-benzo[1,4]dioxin-6-yl)4,5-difluoro-6-(4-iodo-2-methyl-phenylamino)-isophthalamic acid

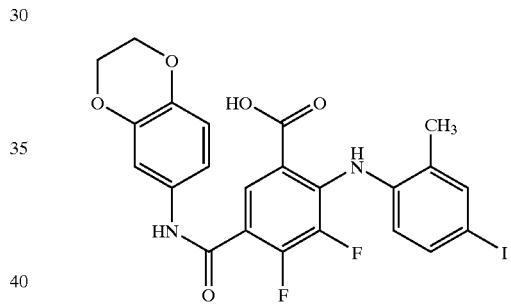

$C_{23}H_{17}F_2IN_2O_5$, MS (APCI)m+1=567
in vitro MEK assay: 65% inhibition @ 1 μM

EXAMPLE 73

3-({1-[5-Carboxy-2,3-difluoro-4-(4-iodo-2-methyl-phenylamino)-phenyl]-methanoyl}-amino)-1H-pyrazole-4-carboxylic acid ethyl ester

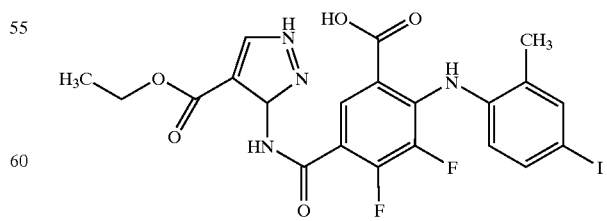

$C_{21}H_{17}F_2IN_4O_5$, MS (APCI)m+1=571
in vitro MEK assay: 86% inhibition @ 1 μM
in vitro MEK assay: $IC_{50}$=1.1 μM

EXAMPLE 74

4,5-Difluoro-6-(4-iodo-2-methyl-phenylamino)-N-pyridin-3-yl-isophthalamic acid

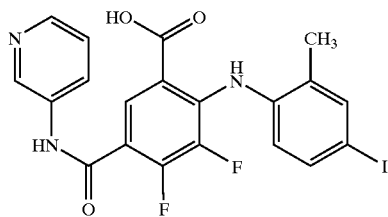

$C_{20}H_{14}F_2IN_3O_3$, MS (APCI)m+1=510
in vitro MEK assay: 50% inhibition @ 1 µM

EXAMPLE 75

1-[3,4-Difluoro-5-[1-(3-hydroxy-piperidin-1-yl)-methanoyl]-2-(4-iodo-2-methyl-phenylamino)-phenyl]-ethanone

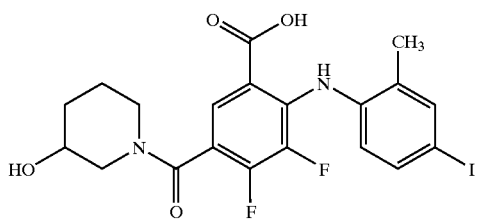

$C_{20}H_{19}F_2IN_2O_4$, MS (APCI)m+1=517
in vitro MEK assay: 92% inhibition @ 1 µM
in vitro MEK assay: $IC_{50}$=0.465 µM

EXAMPLE 76

3,4-Difluoro-5-[1-(3-hydroxymethyl-piperidin-1-yl)-methanoyl]-2-(4-iodo-2-methyl-phenylamino)-benzoic acid

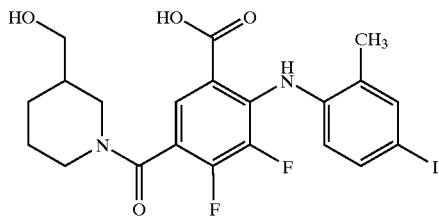

$C_{21}H_{21}F_2IN_2O_4$, MS (APCI)m+1=531
in vitro MEK assay: 88% inhibition @ 1 µM
in vitro MEK assay: $IC_{50}$=0.300 µM

EXAMPLE 77

3,4-Difluoro-5-[1-(3-hydroxy-pyrrolidin-1-yl)-methanoyl]-2-(4-iodo-2-methyl-phenylamino)-benzoic acid

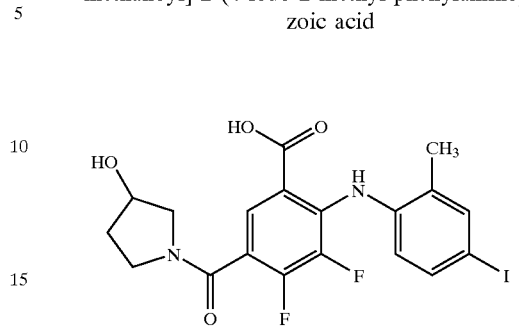

$C_{19}H_{17}F_2IN_2O_4$, MS (APCI)m+1=503
in vitro MEK assay: 83% inhibition @ 1 µM
in vitro MEK assay: $IC_{50}$=0.880 µM

EXAMPLE 78

3,4-Difluoro-2-(4-iodo-2-methyl-phenylamino)-5-[1-(4-pyrrolidin-1-yl-piperidin-1-yl)-methanoyl]-benzoic acid

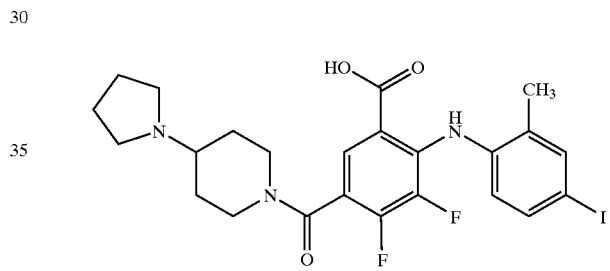

$C_{24}H_{26}F_2IN_3O_3$, MS (APCI)m+1=570
in vitro MEK assay: 33% inhibition @ 1 µM

EXAMPLE 79

4,5-Difluoro-6-(4-iodo-2-methyl-phenylamino)-N-(2-morpholin-4-yl-ethyl)-isophthalamic acid

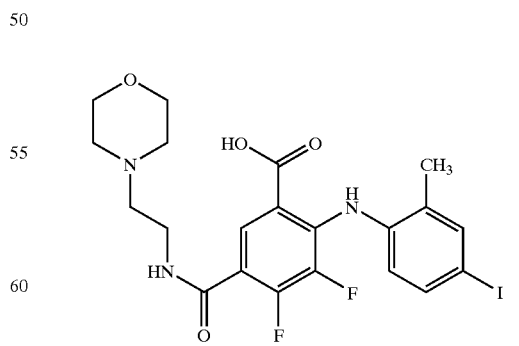

$C_{21}H_{16}F_2IN_3O_4$, MS (APCI)m+1=546
in vitro MEK assay: 54% inhibition @ 1 µM
in vitro MEK assay: $IC_{50}$=1.5 µM

EXAMPLE 80

4,5-Difluoro-6-(4-iodo-2-methyl-phenylamino)-N-pyridin4-ylmethyl-isophthalamic acid

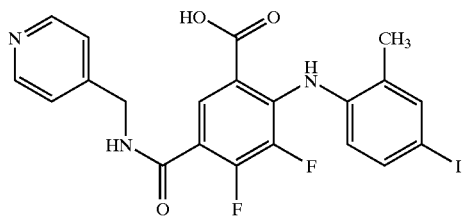

$C_{21}H_{16}F_2IN_3O_3$, MS (APCI)m+1=524
in vitro MEK assay: 71% inhibition 1 μM
in vitro MEK assay: $IC_{50}$=1.7 μM

EXAMPLE 81

3,4-Difluoro-5-[1-(4-hydroxy-piperidin-1-yl)-methanoyl]-2-(4-iodo-2-methyl-phenylamino)-benzoic acid

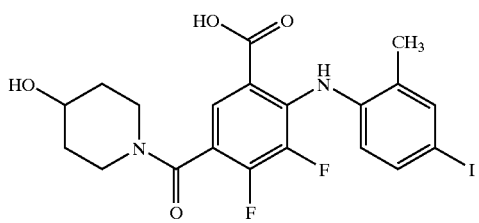

$C_{20}H_{19}F_2IN_2O_4$, MS (APCI)m+1=517
in vitro MEK assay: 86% inhibition @ 1 μM
in vitro MEK assay: $IC_{50}$=1.8 μM

EXAMPLE 82

4,5-Difluoro-6-(4-iodo-2-methyl-phenylamino)-N-(4-morpholin-4-yl-phenyl)-isophthalamic acid $C_{25}H2F_2IN_3O_4$, MS (APCI)m+1=594

EXAMPLE 83

3,4-Difluoro-5-{1-[4-(2-hydroxy-ethyl)-piperidin-1-yl]-methanoyl}-2-(4-iodo-2-methyl-phenylamino)-benzoic acid

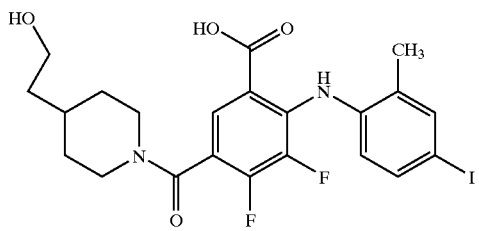

$C_{22}H_{23}F_2IN_2O_4$, MS (APCI)m+1=545
in vitro MEK assay: 90% inhibition @ 1 μM
in vitro MEK assay: $IC_{50}$=0.150 μM

EXAMPLE 84

N-(2-Ethyl-2H-pyrazol-3-yl)-4,5-difluoro-6-(4-iodo-2-methyl-phenylamino)-isophthalamic acid

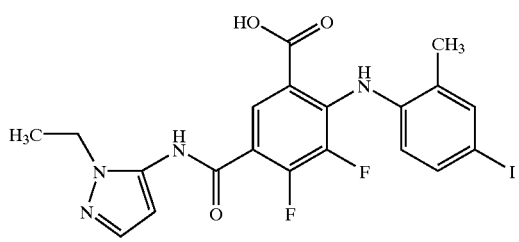

$C_{20}H_{17}F_2IN_4O_3$, MS (APCI)m+1=527
in vitro MEK assay: 79% inhibition @ 1 μM
in vitro MEK assay: $IC_{50}$=0.960 μM

EXAMPLE 85

N-(6-Chloro-pyridin-3-yl)-4,5-difluoro-6-(4-iodo-2-methyl-phenylamino)-isophthalamic acid

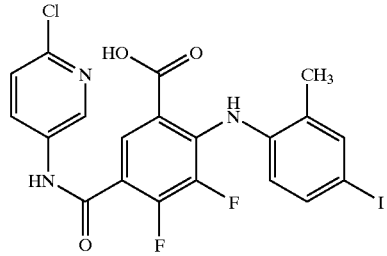

$C_{20}H_{13}F_2IN_3O_3$, MS (APCI)m+1=544
in vitro MEK assay: 90% inhibition @ 1 μM
in vitro MEK assay: $IC_{50}$=0.970 μM

EXAMPLE 86

4,5-Difluoro-N-(1H-indazol-6-yl)-6-(4-iodo-2-methyl-phenylamino)-isophthalamic acid

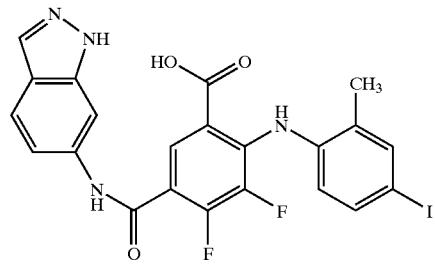

$C_{22}H_{15}F_2IN_4O_3$, MS (APCI)m+1=549
in vitro MEK assay: 77% inhibition @ 1 μM
in vitro MEK assay: $IC_{50}$=1.1 μM

EXAMPLE 87

4,5-Difluoro-N-(2-hydroxy-1-methyl-ethyl)-6-(4-iodo-2-methyl-phenylamino)-isophthalamic acid

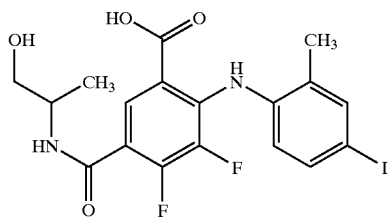

$C_{18}H_{17}F_2IN_2O_4$, MS (APCI)m+1 491
in vitro MEK assay: 66% inhibition @ 1 μM
in vitro MEK assay: $IC_{50}$=2.2 μM

EXAMPLE 88

4,5-Difluoro-N-[2-(1H-imidazol-4-yl)-ethyl]-6-(4-iodo-2-methyl-phenylamino)-isophthalamic acid

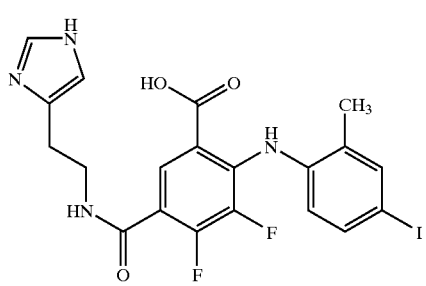

$C_{20}H_{17}F_2IN_4O_3$, MS (APCI)m+1=527
in vitro MEK assay: 60% inhibition @ 1 μM
in vitro MEK assay: $IC_{50}$=1.4 μM

EXAMPLE 89

3,4-Difluoro-2-(4-iodo-2-methyl-1-phenylamino)-5-(1-morpholin-4-yl-methanoyl)-benzoic acid

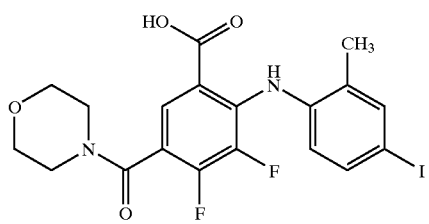

$C_{19}H_{17}F_2IN_2O_4$, MS (APCI)m+1=503
in vitro MEK assay: 89% inhibition @ 1 μM

EXAMPLE 90

4,5-Difluoro-N-(3-imidazol-1-yl-propyl)-6-(4-iodo-2-methyl-phenylamino)-isophthalamic acid

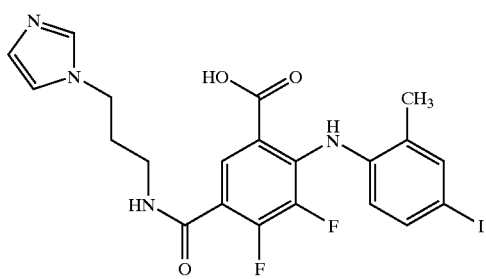

$C_{21}H_{19}F_2IN_4O_3$, MS (APCI)m+1=541
in vitro MEK assay: 59% inhibition @ 1 μM

EXAMPLE 91

4,5-Difluoro-6-(4-iodo-2-methyl-phenylamino)-N-(3-morpholin4-yl-propyl)-isophthalamic acid

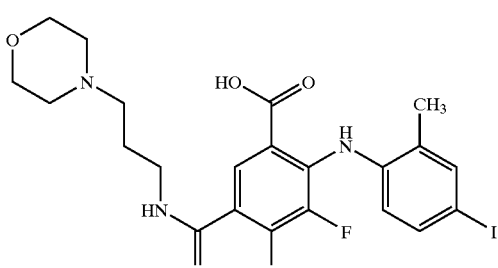

$C_{22}H_{24}F_2IN_3O_4$, MS (APCI)m+1=560
in vitro MEK assay: 58% inhibition @ 1 μM

EXAMPLE 92

N-(4-Dimethylamino-phenyl)-4,5-difluoro-6-(iodo-methyl-phenylamino)-isophthalamic acid

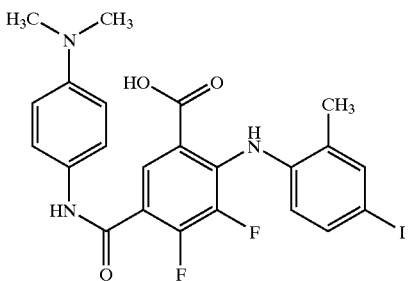

$C_{23}H_{20}F_2IN_3O_3$, MS (APCI)m+1=552
in vitro MEK assay: 80% inhibition @ 1 μM

EXAMPLE 93

5-[1-(4-Ethyl-piperazin-1-yl)-methanoyl]-3,4-difluoro-2-(4-iodo-2-methyl-phenylamino)-benzoic acid

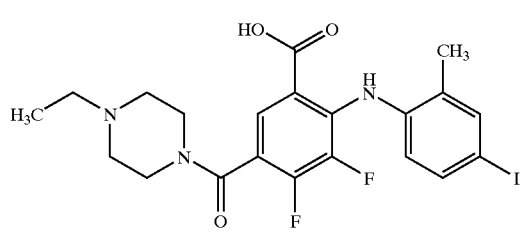

$C_{21}H_{22}F_2IN_3O_3$, MS (APCI)m+1=530
in vitro MEK assay: 70% inhibition @ 1 μM

EXAMPLE 94

4,5-Difluoro-6-(4-iodo-2-methyl-phenylamino)-N-(4-methoxy-phenyl)-N-methyl-isophthalamic acid

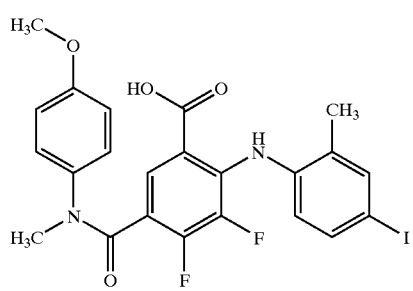

$C_{23}H_{19}F_2IN_2O_4$, MS (APCI)m+1=553
in vitro MEK assay: 92% inhibition @ 1 μM

EXAMPLE 95

4,5-Difluoro-N-[2-(1H-indol-3-yl)-ethyl]-6-(4-iodo-2-methyl-phenylamino)-N-methyl-isophthalamic acid

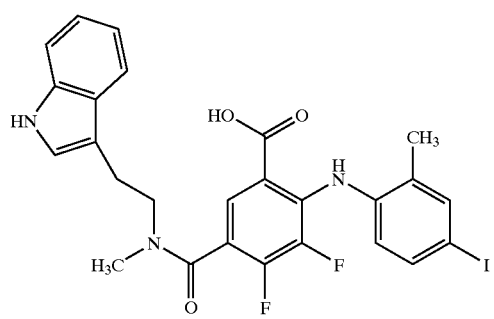

$C_{26}H_{22}F_2IN_3O_3$, MS (APCI)m+1=590
in vitro MEK assay: 77% inhibition @ 1 μM

EXAMPLE 96

4,5-Difluoro-6-(4-iodo-2-methyl-phenylamino)-N-(4-sulfamoyl-phenyl)-isophthalamic acid

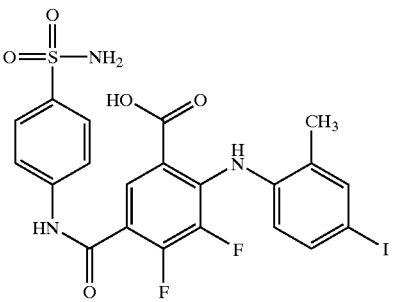

$C_{21}H_{16}F_2IN_3O_4S$, MS (APCI)m+1=588
in vitro MEK assay: 85% inhibition @ 1 μM

EXAMPLE 97

4,5-Difluoro-6-(4-iodo-2-methyl-phenylamino)-N-(tetrahydro-furan-2-ylmethyl)-isophthalamic acid

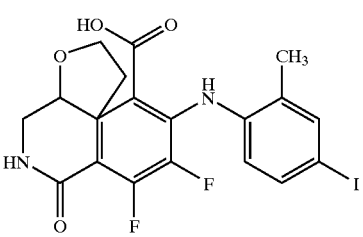

$C_{20}H_{19}F_2IN_2O_4$, MS (APCI)m+1=517
in vitro MEK assay: 81% inhibition @ 1 μM
in vitro MEK assay: $IC_{50}$=0.150 M

EXAMPLE 98

3,4-Difluoro-2-(4-iodo-2-methyl-phenylamino)-5-(1-thiazolidin-3-yl-methanoyl)-benzoic acid

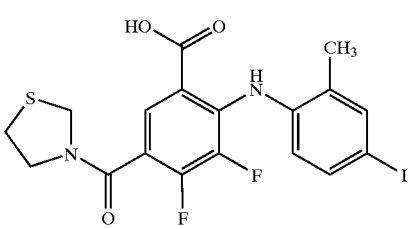

$C_{18}H_{15}F_2IN_2O_3S$, MS (APCI)m+1=505
in vitro MEK assay: 86% inhibition @ 1 μM
in vitro MEK assay: $IC_{50}$=0.087 μM

EXAMPLE 99

3,4-Difluoro-2-(4-iodo-2-methyl-phenylamino)-5-(1-thiomorpholin-4-yl-methanoyl-benzoic acid

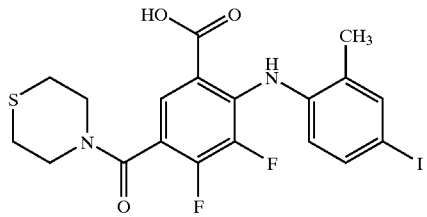

$C_{19}H17F_2IN_2O_3S$, MS (APCI)m+1=519
in vitro MEK assay: 82% inhibition @ 1 μM
in vitro MEK assay: $IC_{50}$=0.150 μM

EXAMPLE 100

4,5-Difluoro-N-((S)-2-hydroxy-cyclohexyl)-6-(4-iodo-2-methyl-phenylamino)-isophthalamic acid

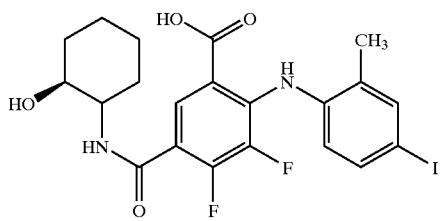

$C_{21}H_{21}F_2IN_2O_4$, MS (APCI)m+1=531

EXAMPLE 101

3,4-Difluoro-5-[1-(3-hydroxy-piperidin-1-yl)-methanoyl]-2-(4-iodo-2-methyl-phenylamino)-benzoic acid

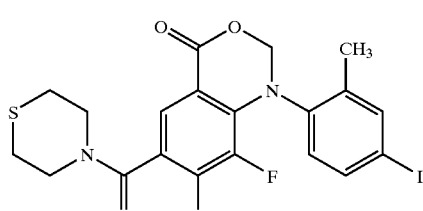

$C_{20}H_{19}F_2IN_2O_4$, MS (APCI)m+1=517
in vitro MEK assay: 75% inhibition @ 1 μM

EXAMPLE 102

4,5-Difluoro-6-(4-iodo-2-methyl-phenylamino-N-(2-piperidin-1-yl-ethyl)-isophthalamic acid

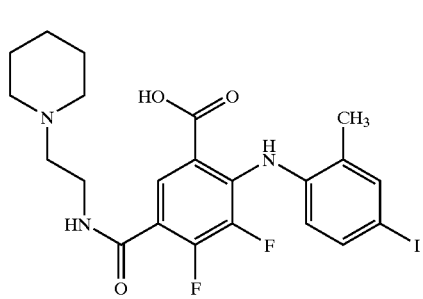

$C22H_{24}F_2IN_3O_3$, MS (APCI)m+1=544
in vitro MEK assay: 25% inhibition @ 1 μM

EXAMPLE 103

3,4-Difluoro-2-(4-iodo-2-methyl-phenylamino)-5-{1-[2-methyl-4-(3-phenoxy-pyridin-4-yl)-piperazin-1-yl]-methanoyl}-benzoic acid

EXAMPLE 104

2-Chloro-4-(4-{1-[2,3-difluoro-4-(4-iodo-2-methyl-phenylamino)-5-carboxy-phenyl]-methanoyl}-3-methyl-piperazin-1-yl)-benzoic acid

EXAMPLE 105

3,4-Difluoro-2-(4-iodo-2-methyl-phenylamino)-5-[1-(4-pyridin-2-yl-piperazin-1-yl)-methanoyl]-benzoic acid

EXAMPLE 106

5-[1-(4-Ethanesulfonyl-piperazin-1-yl)-methanoyl]-3,4-difluoro-2-(4-iodo-2-methyl-phenylamino)-benzoic acid

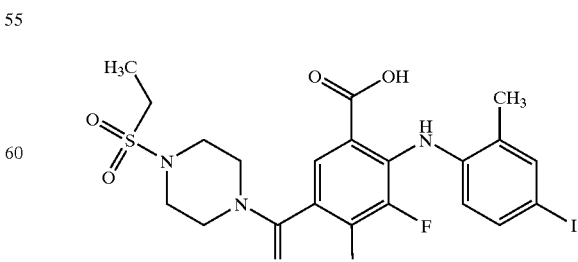

$C_{21}H_{22}F_2IN_3O_35S$, MS (APCI)m+1=594

EXAMPLE 107

5-{1-[3-(2-Amino-ethyl)-2-oxo-imidazolidin-1-yl]-methanoyl}-3,4-difluoro-2-(4-iodo-2-methyl-phenylamino-benzoic acid

EXAMPLE 108

5-{1-[4-(2-Amino-ethyl)-piperazin-1-yl]-methanoyl}-3,4-difluoro-2-(4-iodo-2-methyl-phenylamino)-benzoic acid

EXAMPLE 109

3,4-Difluoro-5-{1-[4-(2-hydroxy-2-methyl-propyl)-piperazin-1-yl]-methanoyl}-2-(4-iodo-2-methyl-phenylamino)-benzoic acid

EXAMPLE 110

5-{1-[4-(2,4-Dimethoxy-phenyl)-piperazin-1-yl]-methanoyl}-3,4-difluoro-2-(4-iodo-2-methyl-phenylamino)-benzoic acid

EXAMPLE 111

5-{1-[4-(2-Carboxy-2-methyl-propyl)-piperazin-1-yl]-methanoyl}-3,4-difluoro-2-(4-iodo-2-methyl-phenylamino)-benzoic acid

EXAMPLE 112

3,4-Difluoro-2-(4-iodo-2-methyl-phenylamino)-5-(1-{4-[3-(propane-1-sulfonyl)-phenyl]-piperazin-1-yl}-methanoyl)-benzoic acid

EXAMPLE 113

3,4-Difluoro-2-(4-iodo-2-methyl-phenylamino)-5-[1-(3'-methyl-2,3,5,6-tetrahydro-[1,2']bipyrazinyl-4-yl)-methanoyl]-benzoic acid

EXAMPLE 114

3,4-Difluoro-2-(4-iodo-2-methyl-phenylamino)-5-[1-(4-{2-[(pyridin-2-ylmethyl)-amino]-ethyl}-piperazin-1-yl)-methanoyl]-benzoic acid

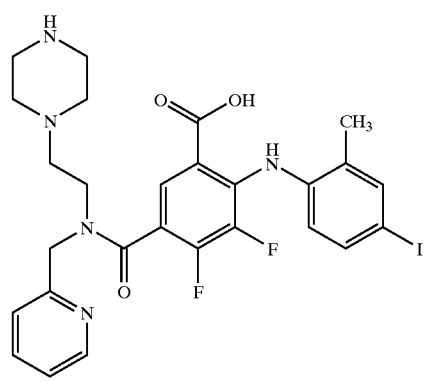

$C_{27}H_{28}F_2IN_5O_3$, MS (APCI)m+1=636

EXAMPLE 115

5-{1-[4-(3-Dimethylamino-propyl)-piperazin-1-yl]-methanoyl}-3,4-difluoro-2-(4-iodo-2-methyl-phenylamino)-benzoic acid

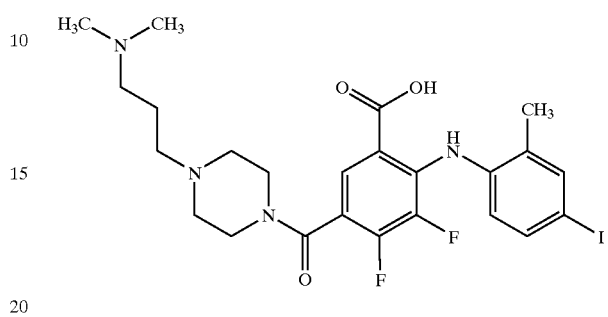

$C_{24}H_{29}F_2IN_4O_3$, MS (APCI)m+1=587

EXAMPLE 116

3,4-Difluoro-5-{1-[4-(6-hydroxy-pyridin-2-yl)-piperazin-1-yl]-methanoyl}-2-(4-iodo-2-methyl-phenylamino)-benzoic acid

EXAMPLE 117

5-(1-{4-[2-(2,5-Dimethyl-pyrrol-1-yl)-ethyl]-piperazin-1-yl}-methanoyl)-3,4-difluoro-2-(4-iodo-2-methyl-phenylamino)-benzoic acid

EXAMPLE 118

3,4-Difluoro-2-(4-iodo-2-methyl-phenylamino)-5-{1-[4-(3-phenoxy-pyridin-2-yl)-piperazin-1-yl]-methanoyl}-benzoic acid

EXAMPLE 119

3,4-Difluoro-2-(4-iodo-2-methyl-phenylamino)-5-{1-[4-(5-phenoxy-pyridin-2-yl)-piperazin-1-yl]-methanoyl}-benzoic acid

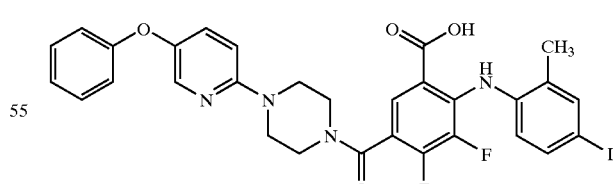

$C_{30}H_{25}F_2IN_4O_4$, MS (APCI)m+1=671

EXAMPLE 120

3,4-Difluoro-2-(4-iodo-2-methyl-phenylamino)-5-{1-[4-(3-phenoxy-pyridin-4-yl)-[1,4]diazepan-1-yl]-methanoyl}-benzoic acid

EXAMPLE 121

5-{1-[4-(3-Chloro-4-hydroxymethyl-phenyl)-piper-azin-1-yl]-methanoyl}-3,4-difluoro-2-(4-iodo-2-methyl-phenylamino)-benzoic acid

EXAMPLE 122

3,4-Difluoro-2-(4-iodo-2-methyl-phenylamino)-5-[1-(8-trifluoromethyl-3,4-dihydro-1H-benzo[4,5]imidazo[1,2-a]pyrazin-2-yl)-methanoyl]-benzoic acid

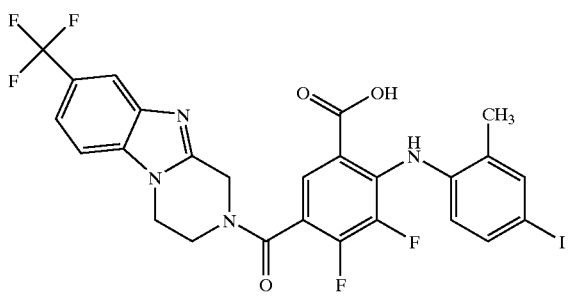

EXAMPLE 123

5-{1-[4-(5-Chloro-1,3-dimethyl-1H-pyrazole-4-sulfonyl)-piperazin-1-yl]-methanoyl}-3,4-difluoro-2-(4-iodo-2-methyl-phenylamino)-benzoic acid

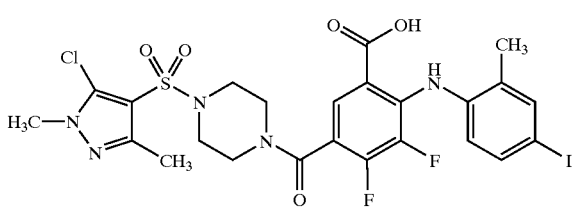

$C_{24}H_{23}ClF_2IN_5O_5S$, MS (APCI)m+1=694

EXAMPLE 124

3,4-Difluoro-5-(1-{4-[2-(2-hydroxy-ethylsulfanyl)-phenyl]-piperazin-1-yl}-methanoyl)-2-(4-iodo-2-methyl-phenylamino)-benzoic acid p0
$C_{19}H_{17}F_2IN_2O_5S$, MS (APCI)m+1=551

EXAMPLE 125

5-[1-(1,1-Dioxo-1$^6$-thiomorpholin-4-yl)-methanoyl]-3,4-difluoro-2-(4-iodo-2-methyl-phenylamino)-benzoic acid

EXAMPLE 126

3,4-Difluoro-2-(4-iodo-2-methyl-phenylamino)-5-{1-[4-(1-methyl-piperidin-4-yl)-piperazin-1-yl]-methanoyl}-benzoic acid

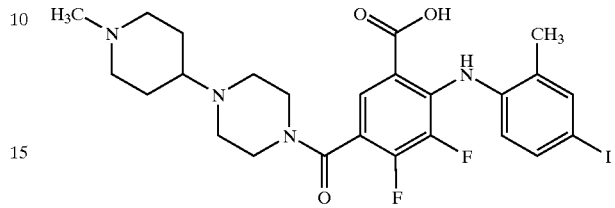

$C_{25}H_{29}F_2IN_4O_3$, MS (APCI)m+1=599

EXAMPLE 127

3,4-Difluoro-2-(4-iodo-2-methyl-phenylamino)-5-[1-(4-oxo-1-phenyl-1,3,8-triaza-spiro[4,5]dec-8-yl)-methanoyl]-benzoic acid

EXAMPLE 128

3,4-Difluoro-5-{1-[4-(2-hydroxy-ethyl)-2,5-dimethyl-piperazin-1-yl]-methanoyl}-2-(4-iodo-2-methyl-phenylamino)-benzoic acid

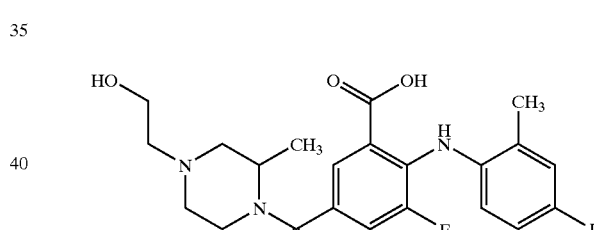

$C_{23}H_{26}F_2IN_3O_4$, MS (APCI)m+1=574

EXAMPLE 129

3,4-Difluoro-5-{1-[4-(2-hydroxy-ethyl)-2,6-dimethyl-piperazin-1-yl]-methanoyl}-2-(4-iodo-2-methyl-phenylamino)-benzoic acid

EXAMPLE 130

3,4-Difluoro-2-(4-iodo-2-methyl-phenylamino)-5-[1-(4-isopropyl-2-methyl-piperazin-1-yl)-methanoyl]-benzoic acid

EXAMPLE 131

5-{1-[4-(3-Chloro-4-hydroxymethyl-phenyl)-2,6-dimethyl-piperazin-1-yl]-methanoyl}-3,4-difluoro-2-(4-iodo-2-methyl-phenylamino)-benzoic acid

EXAMPLE 132

3,4-Difluoro-5-{1-[4-(5-hydroxy-pentyl)-piperazin-1-yl]-methanoyl}-2-(4-iodo-2-methyl-phenylamino)-benzoic acid

EXAMPLE 133

3,4-Difluoro-5-(1-{4-[2-(2-hydroxy-ethoxy)-phenyl]-piperazin-1-yl}-methanoyl)-2-(4-iodo-2-methyl-phenylamino)-benzoic acid

EXAMPLE 134

3,4-Difluoro-2-(4-iodo-2-methyl-phenylamino)-5-{1-[4-(4-methyl-pyridin-2-yl)-piperazin-1-yl]-methanoyl}-benzoic acid

EXAMPLE 135

5-{1-[4-(2-sec-Butoxy-phenyl)-piperazin-1-yl]-methanoyl}3,4-difluoro-2-(4-iodo-2-methyl-phenylamino)benzoic acid

EXAMPLE 136

3,4-Difluoro-2-(4-iodo-2-methyl-phenylamino)-5-{1-[4-(2-isobutoxy-phenyl)-piperazin-1-yl]-methanoyl}-benzoic acid

EXAMPLE 137

5-[1-(4-Benzothiazol-2-yl-piperazin-1-yl)-methanoyl]-3,4-difluoro-2-(4-iodo-2-methyl-phenylamino)-benzoic acid

EXAMPLE 138

5-{1-[4-(6-Ethoxy-pyridin-2-yl)-piperazin-1-yl]-methanoyl}-3,4-difluoro-2-(4-iodo-2-methyl-phenylamino-benzoic acid

EXAMPLE 139

5-[1-(4-Benzooxazol-2-yl-piperazin-1-yl)-methanoyl]-3,4-difluoro-2-(4-iodo-2-methyl-phenylamino)-benzoic acid

EXAMPLE 140

3,4-Difluoro-2-(4-iodo-2-methyl-phenylamino)-5-{1-[4-(3-methyl-quinoxalin-2-yl)-piperazin-1-yl]-methanoyl}-benzoic acid

EXAMPLE 141

5-[1-(3',6'-Dimethyl-2,3,5,6-tetrahydro-[1,2]bipyrazinyl-4-yl)-methanoyl]-3,4-difluoro-2-(4-iodo-2-methyl-phenylamino)-benzoic acid

EXAMPLE 142

3,4-Difluoro-2-(4-iodo-2-methyl-phenylamino)-5-{1-[4-(6-methyl-pyridazin-3-yl)-piperazin-1-yl]-methanoyl}-benzoic acid

EXAMPLE 143

3,4-Difluoro-5-(1-{4-[3-(2-hydroxy-ethoxy)-phenyl]-piperazin-1-yl}-methanoyl)-2-(4-iodo-2-methyl-phenylamino)-benzoic acid

EXAMPLE 144

3,4-Difluoro-5-[1-(2-hydroxy-ethyl)-imidazolidin-2-ylidene-hydrazinocarbonyl]-2-(4-iodo-2-methyl-phenylamino)-benzoic acid

EXAMPLE 145

3,4-Difluoro-2-(4-iodo-2-methyl-phenylamino)-5-(1-{4-[3-(propane-1-sulfonyl)-phenyl]-piperazin-1-yl}-methanoyl)-benzoic acid

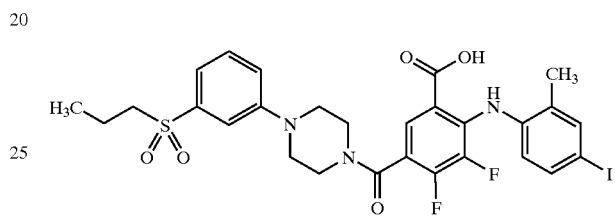

$C_{28}H_{28}F_2IN_3O_5S$, MS (APCI)m+1=684

EXAMPLE 146

3,4-Difluoro-2-(4-iodo-2-methyl-phenylamino)-5-{1-[4-(3-methanesulfonyl-phenyl)-piperazin-1-yl]-methanoyl}-benzoic acid

EXAMPLE 147

3,4-Difluoro-2-(4-iodo-2-methyl-phenylamino)-5-(1-{4-[2-(propane-1-sulfonyl)-phenyl]-piperazin-1-yl}-methanoyl)-benzoic acid

EXAMPLE 148

5-{1-[4-(4,5-Dimethyl-thiazol-2-yl)-piperazin-1-yl]-methanoyl}-3,4-difluoro-2-(4-iodo-2-methyl-phenylamino)-benzoic acid

EXAMPLE 149

5-{1-[4-(5-Ethyl-[1,3,4]thiadiazol-2-yl)-piperazin-1-yl]-methanoyl}-3,4-difluoro-2-(4-iodo-2-methyl-phenylamino)-benzoic acid

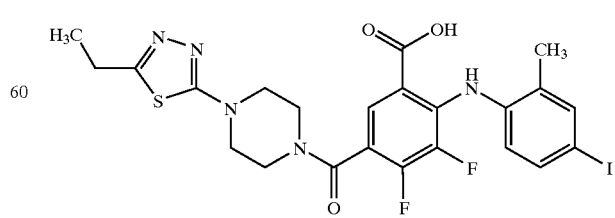

$C_{23}H22F_2IN_5O_3S$, MS (APCI)m+1=614

EXAMPLE 150

3,4-Difluoro-5-{1-[4-(1-furan-2-yl-methanoyl)-piperazin-1-yl]-methanoyl}-2-(4-iodo-2-methyl-phenylamino)-benzoic acid

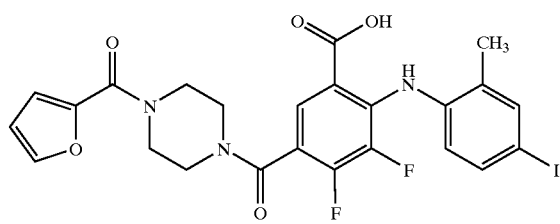

$C_{24}H_{20}F_2IN_3O_5$, MS (APCI)m+1=596

EXAMPLE 151

5-(1-{4-[4-(4,5-Dihydro-1H-imidazol-2-yl)-butyl]-piperazin-1-yl}-methanoyl)-3,4-difluoro-2-(4-iodo-2-methyl-phenylamino)-benzoic acid

EXAMPLE 152

3,4-Difluoro-2-(4-iodo-2-methyl-phenylamino)-5-{1-[4-(3-phosphono-propyl)-piperazin-1-yl]-methanoyl}-benzoic acid

EXAMPLE 153

3,4-Difluoro-5-{1-[4-(2-hydroxy-ethyl)-piperazin-1-yl]-methanoyl}-2-(4-iodo-2-methyl-phenylamino)-benzoic acid

EXAMPLE 154

3,4-Difluoro-2-(4-iodo-2-methyl-phenylamino)-5-[1-(5-methyl-hexahydro-pyrrolo[3,4-c]pyrrol-2-yl)-methanoyl]-benzoic acid

EXAMPLE 155

N-(1,1-Dioxo-tetrahydro-11⁶-thiophen-3-yl)-4,5-difluoro-6-(4-iodo-2-methyl-phenylamino)-N-methyl-isophthalamic acid

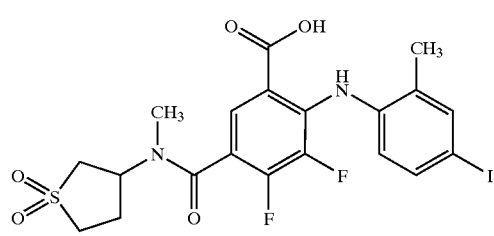

$C_{20}H_{19}F_2IN_2O_5S$, MS (APCI)m+1=565

EXAMPLE 156

3-({1-[5-Carboxy-2,3-difluoro-4-(4-iodo-2-methyl-phenylamino)-phenyl]-methanoyl}-amino)-tetrahydro-thiophene-3-carboxylic acid

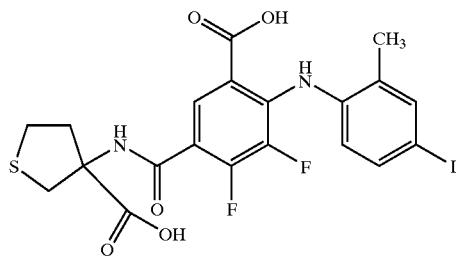

EXAMPLE 157

4,5-Difluoro-N-(1-hydroxymethyl-cyclopentyl)-6-(4-iodo-2-methyl-phenylamino)-isophthalamic acid

EXAMPLE 158

4,5-Difluoro-N-(4-hydroxy-cyclohexyl)-6-(4-iodo-2-methyl-phenylamino)-isophthalamic acid

EXAMPLE 159

4,5-Difluoro-N-((R)-2-hydroxy-cyclohexyl)-6-(4-iodo-2-methyl-phenylamino)-isophthalamic acid

EXAMPLE 160

N-(3-Cyclohexylamino-propyl)-4,5-difluoro-6-(4-iodo-2-methyl-phenylamino)-isophthalamic acid

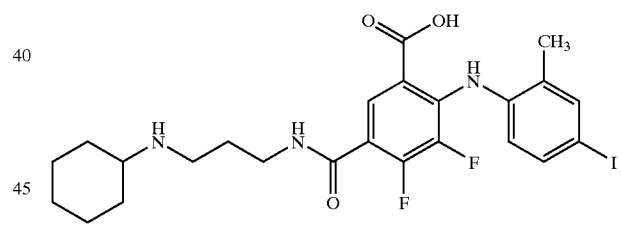

$C_{24}H_{28}F_2IN_3O_3$, MS (APCI)m+1=572

EXAMPLE 161

4,5-Difluoro-6-(4-iodo-2-methyl-phenylamino)-N-(2-methylene-tetrahydro-thiophen-3-yl)-isophthalamic acid

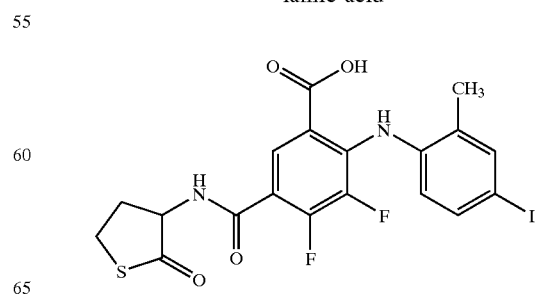

$C_{19}H_{15}F_2IN_2O_4S$, MS (APCI)m+1=533

EXAMPLE 162

N-(1,1-Dioxo-tetrahydro-11$^6$-thiophen-3-yl)-4,5-difluoro-6-(4-iodo-2-methyl-phenylamino)-isophthalamic acid

BIOLOGICAL EXAMPLES

EXAMPLE 163

Cascade Assay for Inhibitors of the MAP Kinase Pathway

Incorporation of $^{32}$P into myelin basic protein (MBP) is assayed in the presence of a glutathione S-transferase fusion protein containing p44MAP kinase (GST-MAPK) and a glutathione S-transferase fusion protein containing p45MEK (GST-MEK). The assay solution contains 20 mM HEPES, pH 7.4, 10 mM MgCl$_2$, 1 mM MnCl$_2$, 1 mM EGTA, 50 µM [γ-$^{32}$P]ATP, 10 µg GST-MEK, 0.5 µg GST-MAPK and 40 µg MBP in a final volume of 100 µL. Reactions are stopped after 20 minutes by addition of trichloroacetic acid and filtered through a GF/C filter mat. $^{32}$P retained on the filter mat is determined using a 120S Betaplate. Compounds are assessed at 10 µM for ability to inhibit incorporation of $^{32}$P.

To ascertain whether compounds are inhibiting GST-MEK or GST MAPK, two additional protocols are employed. In the first protocol, compounds are added to tubes containing GST-MEK, followed by addition of GST-MAPK, MBP and [γ-$^{32}$P]ATP. In the second protocol, compounds are added to tubes containing both GST-MEK and GST-MAPK, followed by MBP and [γ-$^{32}$P]ATP.

Compounds that show activity in both protocols are scored as MAPK inhibitors, while compounds showing activity in only the first protocol are scored as MEK inhibitors.

EXAMPLE 164

In Vitro MAP Kinase Assay

Inhibitory activity can be confirmed in direct assays. For MAP kinase, 1 µg GST-MAPK is incubated with 40 µg MBP in the presence or absence of test compound for 15 minutes at 30° C. in a final volume of 50 µL containing 50 mM Tris (pH 7.5), 10 µM MgCl$_2$, 2 µM EGTA, and 10 µM [γ-$^{32}$P] ATP. The reaction is stopped by addition of Laemmli SDS sample buffer and phosphorylated MBP resolved by electrophoresis on a 10% polyacrylamide gel. Radioactivity incorporated into MBP is determined by both autoradiography, and scintillation counting of excised bands.

EXAMPLE 165

In Vitro MEK Assay

For evaluation of direct MEK activity, 10 µg GST-MEK, is incubated in the presence of absence of test compound with 5 µg of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations are 15 minutes at 30° C. in a final volume of 50 µL containing 50 mM Tris (pH 7.5), 10 µM MgCl$_2$, 2, µM EGTA, and 10 µM [γ-$^{32}$P]ATP. The reaction is stopped by addition of Laemmli SDS sample buffer. Phosphorylated GST-MAPK-KA is resolved by electrophoresis on a 10% polyacrylamide gel. Radioactivity incorporated into GST-MAPK-KA is determined by autoradiography, and subsequent scintillation counting of excised bands.

Alternatively, an artificially activated MEK containing serine to glutamate mutations at positions 218 and 222 (GST-MEK-2E) is used. When these two sites are phosphorylated, MEK activity is increased. Phosphorylation of these sites can be mimicked by mutation of the serine residues to glutamate. For this assay, 5 µg GST-MEK-2E is incubated with 5 µg GST-MAPK-KA for 15 minutes at 30° C. in the same reaction buffer as described above. Reactions are terminated and analyzed as above.

EXAMPLE 166

Whole Cell MAP Kinase Assay

To determine if compounds block activation of MAP kinase in whole cells, the following protocol is used. Cells are plated in multi-well plates and grown to confluence. Cells are serum-deprived overnight. Cells are exposed to the desired concentrations of compound or vehicle (DMSO) for 30 minutes, followed by addition of a growth factor, for example, PDGF (100 ng/mL). After a 5-minute treatment with the growth factor, cells are washed with PBS, and lysed in a buffer consisting of 70 mM NaCl, 10 mM HEPES (pH 7.4), 50 mM glycerol phosphate, and 1% Triton X-100. Lysates are clarified by centrifugation at 13,000×g for 10 minutes. Five micrograms of the resulting supernatants are incubated with 10 µg microtubule associated protein-2 (Map2) for 15 minutes at 30° C. in a final volume of 25 µL containing 50 mM Tris (pH 7.4), 10 mM MgCl$_2$, 2 mM EGTA and 30 µM [γ-$^{32}$P]ATP. Reactions are terminated by addition of Laermmli sample buffer. Phosphorylated Map2 is resolved on 7.5% acrylamide gels and incorporated radioactivity is determined by scintillation counting of excised bands.

EXAMPLE 167

Monolayer Growth

Cells are plated into multi-well plates at 10 to 20,000 cells/mL. Forty-eight hours after seeding, test compounds are added to the cell growth medium and incubation is continued for 2 additional days. Cells are then removed from the wells by incubation with trypsin and enumerated with a Coulter counter.

EXAMPLE 168

Growth in Soft-Agar

Cells are seeded into 35-mm dishes at 5 to 10,000 cells/dish using growth medium containing 0.3% agar. After chilling to solidify the agar, cells are transferred to a 37° C. incubator. After 7 to 10 days' growth, visible colonies are manually enumerated with the aid of a dissecting microscope.

EXAMPLE 169

Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 µg type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type 11 collagen, and there is a marked cellular response to CII.

EXAMPLE 170

SCW-induced Monoarticular Arthritis

Arthritis is induced as described by Schwab, et al., *Infection and Immunity*, 59:4436–4442 (1991) with minor modifications. Rats receive 6 µg sonicated SCW [in 10 µl Dulbecco's PBS (DPBS)] by an intraarticular injection into the right tibiotalar joint on day 0. On day 21, the DTH is initiated with 100 µg of SCW (250 µl) administered i.v. For oral compound studies, compounds are suspended in vehicle (0.5% hydroxypropyl-methylcellulose/0.2% Tween 80), sonicated, and administered twice daily (10 ml/kg volume) beginning 1 hr prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on day 21, and comparing them with volumes at subsequent time points such as day 22, 23, 24, and 25. Paw volume is determined by mercury plethysmography.

EXAMPLE 171

Mouse Ear-heart Transplant Model

Fey, T. A. et al. describe methods for transplanting split-heart neonatal cardiac grafts into the ear pinna of mice and rats (*J. Pharm. and Toxic. Meth.* 39:9–17 (1998)). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (day 0) through day 13 or until grafts have been rejected. Rats are dosed once, twice, or three times daily from day 0 through day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10–20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1–4 times a day for 10, 20, 30 or more days. The ability of a test compound to ameliorate symptoms of transplant rejection can be compared with a control compound such as cyclosporine, tacrolimus, or orally-administered lefluonomide.

EXAMPLE 172

Murine Ovalbumin-induced Eosinolphilia

Female C57BL/6 mice are obtained from the Jackson Laboratory (Bar Harbor, Me.). All animals are given food and water ad libitum. Mice are sensitized with a single i.p. injection of OVA (grade V, Sigma Chemical Company, St. Louis, Mo.) adsorbed to alum, (10 µg OVA+9 mg alum in 200 µl saline) or vehicle control, (9 mg alum in 200 µl saline) on day 0. On day 14, the mice are challenged with a 12-minute inhalation of an aerosol consisting of 1.5% OVA (weight/volume) in saline produced by a nebulizer (small particle generator, model SPAG-2; ICN Pharmaceuticals, Costa Mesa, Calif.). Groups of eight mice are dosed with oral vehicle (0.5% hydroxypropylmethylcellulose/0.25% TWEEN-80), or a test compound at 10, 30, or 100 mg/kg in oral vehicle, 200 µl per mouse p.o. Dosing is performed once per day starting on day 7 or day 13, and extending through day 16.

For determination of pulmonary eosinophilia, three days after the first OVA aerosol challenge (day 17), the mice are anesthetized with an i.p. injection of anesthetic (Ketamine/Acepromazine/Xylazine), and the tracheae is exposed and cannulated. The lungs and upper airways are lavaged twice with 0.5 ml of cold PBS. A portion (200 µl) of the bronchoalveolar lavage (BAL) fluid is enumerated using a Coulter counter Model ZB1 (Coulter Electronics, Hialeah, Fla.). The remaining BAL fluid is then centrifuged at 300×g for five minutes, and the cells are resuspended in 1 ml of HBSS (Gibco BRL) containing 0.5% fetal calf serum (HyClone) and 10 mM HEPES (Gibco BRL). The cell suspension is centrifuged in a cytospin (Shandon Southern Instruments, Sewickley, Pa.) and stained by Diff Quick (American Scientific Products, McGraw Park, Ill.) to differentiate BAL leukocytes into neutrophil, eosinophil, monocyte or lymphocyte subsets. The number of eosinophils in the BAL fluid is determined by multiplying the percentage of eosinophils by the total cell count.

EXAMPLE 173

Experimental compounds are added to 96 well format plates with filter bottomed wells. Kinase-inactive ERK1 (K71R mutant) in HEPES buffer is then added to each well. After subsequent addition of MEK1 (2D mutant) diluted in a Tris buffer before being added to the plate, and the reaction is initiated by the addition of radioactive ATP, diluted in 0.05% Tween 20. After 1 hour incubation at room temperature, Ice-cold 20% TCA is added to each well to stop the reaction and to precipitate the protein in solution. Filtration is done the following day by scintillation counting of the incorporated radioactivity using a Perkin Elmer Wallac microBeta 1450 counter. Inhibition is expressed as a percentage of the vehicle control.

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:

1. A compound of formula I:

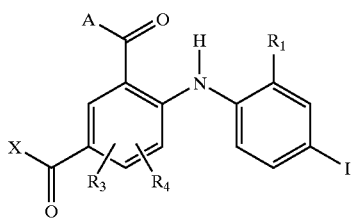

I or the pharmaceutically acceptable salts thereof;
wherein
$R_1$ is hydrogen, $C_{1-8}$ alkyl, $C_{1-8}$ alkoxy, halo, $C_{1-2}$ haloalkyl, or CN;
$R_3$ and $R_4$ are each independently hydrogen, halo, $C_{1-2}$ haloalkyl, $C_{1-8}$ alkyl, $C_{1-8}$ alkoxy, nitro, CN, or (O or NH)$_k$—(CH$_2$)$_j$—$R_9$, where $R_9$ is hydrogen, hydroxy, CO$_2$H or NR$_{10}$R$_{11}$;
j is 0 to 4;
k is 0 or 1;
$R_{10}$ and $R_{11}$ are each independently hydrogen or $C_{1-8}$ alkyl, or together with the nitrogen to which they are attached form a 3- to 10-member cyclic ring optionally containing one, two, or three additional heteroatoms selected from the group consisting of O, S, NH, and N—$C_{1-8}$ alkyl;
A is hydroxy, $C_{1-6}$ alkoxy, or NR$_6$OR$_7$;
$R_6$ is hydrogen, $C_{1-8}$ alkyl, (CO)—$C_{1-8}$ alkyl, phenyl, naphthyl, phenyl($C_{1-8}$ alkyl), or $C_{3-10}$ cycloalkyl;
$R_7$ is hydrogen, $C_{1-8}$ alkyl, $C_{2-8}$ alkenyl, $C_{2-8}$ alkynyl, $C_{3-10}$ cycloalkyl or $C_{3-10}$ cycloalkyl optionally containing a heteroatom selected from the group consisting of O, S, and NR$_9$;
X is NR$_{13}$R$_{12}$, or NR$_{14}$;
$R_{12}$ and $R_{13}$ are each independently hydrogen, $C_{1-6}$ alkyl, $C_{2-6}$ alkenyl, $C_{2-6}$ alkynyl, $C_{4-6}$ cycloalkyl, [(CH$_2$)$_n$Y(CH$_2$)$_m$]$_q$CH$_3$, phenyl, naphthyl, ($C_{1-6}$ alkyl)phenyl, —[(CH$_2$)$_n$Y(CH$_2$)$_m$]$_q$phenyl, $C_{2-6}$ heteroaryl, ($C_{1-6}$ alkyl)$C_{2-6}$ heterocyclic radical, or [(CH$_2$)$_n$Y(CH$_2$)$_m$]$_q$ $C_{2-6}$ heterocyclic radical;
Y is NH or O;
$R_{14}$ taken with N is a 5- to 7-membered heterocyclic radical with between 0 and 3 additional heteroatoms or heteroatom combinations in the ring selected from the group consisting of O, S, SO, SO$_2$, NH, and NMe;

$0 \leq n$, $m \leq 6$, $n+m \leq 8$, $1 \leq q \leq 5$; and wherein the above alkyl, alkenyl, alkynyl, heterocyclic radical, aryl, and cycloalkyl groups can be optionally substituted with between 1 and 4 substituents independently selected from the group consisting of hydroxy, $C_{1-4}$ alkyl, fluoro, chloro, iodo, bromo, amino, and $C_{1-4}$ alkoxy, and NR$_a$R$_b$;
wherein $R_a$ and $R_b$ are each independently selected from the group consisting of hydrogen and $C_{1-6}$ alkyl.

2. A compound of claim 1 wherein $R_1$ is $C_{1-8}$ alkyl or halo.

3. A compound of claim 2 wherein $R_1$ is methyl.

4. A compound of claim 1 wherein $R_3$ and $R_4$ are each independently selected from the group consisting of hydrogen and halo.

5. A compound of claim 4 wherein halo is fluoro.

6. A compound of claim 1 wherein A is NR$_6$OR$_7$.

7. A compound of claim 1 wherein X is NR$_{13}$R$_{12}$.

8. A compound of claim 1 wherein X is NR$_{14}$.

9. A compound of claim 1 wherein $R_{12}$ and $R_{13}$ are each independently selected from the group consisting of [(CH$_2$)$_n$Y(CH$_2$)$_m$]$_q$CH$_3$, ($C_{1-6}$ alkyl)phenyl, —[(CH$_2$)$_n$Y(CH$_2$)$_m$]$_q$phenyl, and ($C_{1-6}$ alkyl)$C_{2-6}$ heterocyclic radical.

10. A compound of claim 1 wherein the heterocyclic radical is a heteroaryl selected from the group consisting of a substituted or unsubstituted radical of pyrrole, furan, pyran, thiophene, pyrazole, imidazole, triazole, tetrazole, indole, isoxazole, indazole, pyridine, pyrazine, oxazole, thiazole, oxadiazole, and oxathiadiazole.

11. A compound of claim 1 wherein the heterocyclic radical is a heteroalkyl selected from the group consisting of a substituted or unsubstituted radical of morpholine, piperidine, piperazine, tetrahydrofuran, tetrahydropyran, pyrrolidone, imidazoline, and tetrahydrothiophene.

12. The compound according to claim 1 where Y is O.

13. A pharmaceutical composition comprising a compound of claim 1 and a pharmaceutically acceptable carrier.

14. A method of treating psoriasis in a patient in need thereof comprising administering a therapeutically effective amount of a compound of claim 1.

15. A method of treating osteoarthritis in a patient in need thereof comprising administering a therapeutically effective amount of a compound of claim 1.

16. A method of treating rheumatoid arthritis in a patient in need thereof comprising administering a therapeutically effective amount of a compound of claim 1.

17. The method of any of claims 14, 15, 16, wherein Y is O.

* * * * *